US012740717B2

(12) United States Patent
Valdez

(10) Patent No.: US 12,740,717 B2
(45) Date of Patent: Sep. 22, 2026

(54) SHUNT IMPLANT DEVICES WITH OVER-CHANNEL SENSOR ARMS

(71) Applicant: EDWARDS LIFESCIENCES CORPORATION, Irvine, CA (US)

(72) Inventor: Michael G. Valdez, Riverside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 222 days.

(21) Appl. No.: 18/466,670

(22) Filed: Sep. 13, 2023

(65) Prior Publication Data

US 2023/0414117 A1 Dec. 28, 2023

Related U.S. Application Data

(63) Continuation of application No. PCT/US2022/018748, filed on Mar. 3, 2022.

(60) Provisional application No. 63/161,385, filed on Mar. 15, 2021.

(51) Int. Cl.

| | |
|---|---|
| ***A61B 5/00*** | (2006.01) |
| ***A61B 5/0215*** | (2006.01) |
| ***A61M 27/00*** | (2006.01) |

(52) U.S. Cl.

CPC .......... *A61B 5/0215* (2013.01); *A61B 5/0031* (2013.01); *A61B 5/6869* (2013.01); *A61B 5/6882* (2013.01); *A61M 27/002* (2013.01)

(58) Field of Classification Search

None

See application file for complete search history.

(56) References Cited

U.S. PATENT DOCUMENTS

| | | | | |
|---|---|---|---|---|
| 5,199,428 | A | 4/1993 | Obel et al. | |
| 6,309,350 | B1 | 10/2001 | Vantassel et al. | |
| 6,616,675 | B1 * | 9/2003 | Evard ................ | A61B 18/1445 606/155 |
| 6,783,499 | B2 | 8/2004 | Schwartz | |
| 7,340,288 | B1 | 3/2008 | Karicherla et al. | |
| 7,389,142 | B2 | 6/2008 | Holmstroem | |

(Continued)

FOREIGN PATENT DOCUMENTS

| | | |
|---|---|---|
| CN | 101271029 A | 9/2008 |
| CN | 105193529 A | 12/2015 |

(Continued)

OTHER PUBLICATIONS

Abraham W.T., et al., "V-LAP Left Atrial Monitoring systEm for Patients with Chronic sysTOlic and Diastolic Congestive Heart Failure First-in-Human," Journal of Cardial Failure, Churchill Livingstone, Naperville, IL, US, Aug. 1, 2019, vol. 25, No. 8S, pp. S74-S75 (2 Pages).

(Continued)

*Primary Examiner* — Meredith Weare

(74) *Attorney, Agent, or Firm* — Chang and Hale LLP

(57) ABSTRACT

A sensor implant device can include a shunt body that forms a fluid conduit, a first anchor structure associated with a first axial end of the shunt body, a second anchor structure associated with a second axial end of the shunt body, and a first sensor device coupled to the first anchor structure, the first anchor structure being configured to hold the first sensor device in a sensing position over a channel area of the fluid conduit.

22 Claims, 22 Drawing Sheets

(56) References Cited

U.S. PATENT DOCUMENTS

| | | | | |
|---|---|---|---|---|
| 7,452,334 | B2 | 11/2008 | Gianchandani et al. | |
| 8,175,668 | B1 | 5/2012 | Nabutovsky et al. | |
| 8,929,982 | B2 | 1/2015 | Holmstrom et al. | |
| 9,999,528 | B2 | 6/2018 | Kim et al. | |
| 10,806,352 | B2 | 10/2020 | Sweeney et al. | |
| 11,039,924 | B2 | 6/2021 | Yaron | |
| 11,234,702 | B1 * | 2/2022 | Eigler | A61B 5/6862 |
| 2002/0151816 | A1 | 10/2002 | Rich et al. | |
| 2005/0065589 | A1 | 3/2005 | Schneider et al. | |
| 2005/0267478 | A1 | 12/2005 | Corradi et al. | |
| 2006/0020324 | A1 | 1/2006 | Schmid et al. | |
| 2006/0161171 | A1 | 7/2006 | Schwartz | |
| 2007/0021665 | A1 | 1/2007 | Hettrick et al. | |
| 2007/0129637 | A1 | 6/2007 | Wolinsky et al. | |
| 2008/0051863 | A1 | 2/2008 | Schneider et al. | |
| 2008/0082005 | A1 | 4/2008 | Stern et al. | |
| 2009/0024042 | A1 | 1/2009 | Nunez et al. | |
| 2009/0248105 | A1 | 10/2009 | Keilman et al. | |
| 2010/0179449 | A1 | 7/2010 | Chow et al. | |
| 2011/0288436 | A1 | 11/2011 | Stone | |
| 2012/0022507 | A1 | 1/2012 | Najafi et al. | |
| 2012/0116489 | A1 | 5/2012 | Khairkhahan et al. | |
| 2012/0239142 | A1 | 9/2012 | Liu et al. | |
| 2012/0259217 | A1 | 10/2012 | Gerrans et al. | |
| 2012/0265296 | A1 | 10/2012 | McNamara et al. | |
| 2012/0296418 | A1 * | 11/2012 | Bonyuet | A61F 2/2415 623/2.18 |
| 2013/0046152 | A1 | 2/2013 | Najafi et al. | |
| 2013/0165967 | A1 | 6/2013 | Amin et al. | |
| 2013/0281774 | A1 | 10/2013 | Honaryar et al. | |
| 2013/0338763 | A1 | 12/2013 | Rowe et al. | |
| 2014/0107722 | A1 | 4/2014 | Kaiser et al. | |
| 2014/0155768 | A1 | 6/2014 | Orion et al. | |
| 2014/0163449 | A1 * | 6/2014 | Rottenberg | A61B 17/00234 604/9 |
| 2014/0214149 | A1 | 7/2014 | Kuraguntla et al. | |
| 2015/0025612 | A1 | 1/2015 | Haasl et al. | |
| 2015/0112383 | A1 | 4/2015 | Sherman et al. | |
| 2015/0157268 | A1 | 6/2015 | Winshtein et al. | |
| 2015/0351648 | A1 | 12/2015 | Harvey et al. | |
| 2016/0045165 | A1 | 2/2016 | Braido et al. | |
| 2016/0045316 | A1 | 2/2016 | Braido et al. | |
| 2016/0157868 | A1 | 6/2016 | Tillman et al. | |
| 2016/0256141 | A1 | 9/2016 | Mendez et al. | |
| 2016/0338823 | A1 | 11/2016 | Akingba | |
| 2017/0095163 | A1 | 4/2017 | Bitzer et al. | |
| 2017/0319067 | A1 | 11/2017 | Najafi | |
| 2018/0071542 | A1 | 3/2018 | Nyberg et al. | |
| 2018/0098772 | A1 | 4/2018 | Goldshtein et al. | |
| 2018/0140444 | A1 | 5/2018 | Neuss et al. | |
| 2018/0168460 | A1 | 6/2018 | Morris et al. | |
| 2019/0083801 | A1 | 3/2019 | Yang et al. | |
| 2019/0343388 | A1 | 11/2019 | Bahmanyar et al. | |
| 2020/0054867 | A1 | 2/2020 | Schwartz et al. | |
| 2020/0094048 | A1 | 3/2020 | Regnier et al. | |
| 2020/0155014 | A1 | 5/2020 | Arthur et al. | |
| 2020/0196944 | A1 | 6/2020 | Minor et al. | |
| 2020/0197178 | A1 * | 6/2020 | Vecchio | A61B 5/021 |
| 2020/0289257 | A1 | 9/2020 | Marquez et al. | |
| 2021/0000581 | A9 | 1/2021 | Eigler et al. | |
| 2021/0045691 | A1 * | 2/2021 | Zou | A61B 5/686 |
| 2021/0121130 | A1 | 4/2021 | Nagy et al. | |
| 2021/0177277 | A1 | 6/2021 | Cros et al. | |
| 2022/0008014 | A1 * | 1/2022 | Rowe | A61B 5/0215 |
| 2022/0151618 | A1 * | 5/2022 | Eigler | A61F 2/2418 |
| 2024/0090842 | A1 * | 3/2024 | Chang | A61B 5/6862 |

FOREIGN PATENT DOCUMENTS

| | | | | |
|---|---|---|---|---|
| CN | 111317516 A | 6/2020 | | |
| EP | 2338420 A1 | 6/2011 | | |
| WO | WO-2007057739 A1 | 5/2007 | | |
| WO | WO-2007058872 A2 | 5/2007 | | |
| WO | WO-2012031204 A2 | 3/2012 | | |
| WO | WO-2016178171 A1 | 11/2016 | | |
| WO | WO-2018213320 A1 | 11/2018 | | |
| WO | WO-2020123338 A1 | * | 6/2020 | A61B 5/6862 |
| WO | WO-2020163112 A1 | * | 8/2020 | A61F 2/2478 |
| WO | WO-2021015929 A1 | 1/2021 | | |
| WO | WO-2021050589 A1 | 3/2021 | | |
| WO | WO-2021113449 A1 | 6/2021 | | |
| WO | WO-2022046425 A1 | 3/2022 | | |
| WO | WO-2022046473 A1 | 3/2022 | | |
| WO | WO-2022051716 A1 | 3/2022 | | |
| WO | WO-2023177824 A1 | 9/2023 | | |

OTHER PUBLICATIONS

Chow E.Y., et al., "Toward an Implantable Wireless Cardiac Monitoring Platform Integrated with an FDA-Approved Cardiovascular Stent," Journal of Interventional Cardiology, 2009, vol. 22, No. 5, pp. 479-487, Wiley Periodicals, Inc., Hoboken, New Jersey.

Hur T., et al., "Improving Structural Strength and Stability of Parylene-based Capacitive Micro Pressure Sensor Using Corrugated Sidewall", MEMS 2019, Jan. 2019, pp. 727-730. I XP093213755, Retrieved from the Internet: URL:https://ieeexplore.ieee.org/stampPDF/getPDF.jsp?tp=&arnumber=8870736&ref=aHR0cHM6Ly9zY2hvbGFyLmdvb2dsZSSjb20v figures 1-6.

Kim A., et al., "An Implantable Pressure Sensing System With Electromechanical Interrogation Scheme," IEEE Transactions on Biomedical Engineering, IEEE, USA, Jul. 1, 2014, vol. 61(7), pp. 2209-2217, DOI: 10.1109/TBME.2014.2318023, ISSN 0018-9294, XP011551241, (Jun. 16, 2014).

Neema P.K., et al., "Left Atrial Pressure Waveform: Does It Show Mitral Insufficiency," Journal of Cardiothoracic and Vascular Anesthesia, Diagnostic Dilemmas, Elsevier, Amsterdam, NL, Apr. 2008, vol. 22, No. 2, pp. 318-320, Mar. 28, 2008.

Nitter-Hauge S., et al., "Clinical and Hemodynamic Results After Combined Aortic and Mitral Valve Replacement With the Lillehei-Kaster Pivoting Disc Valve," Experimental and Laboratory Reports, American Heart Journal, May 1, 1979, vol. 97, No. 5, pp. 599-607.

O'Rourke R.A., et al., "Mitral Valve Regurgitation," Current Problems in Cardiology, May 1, 1984, vol. 9, No. 3, pp. 1-52.

Snyder R.W.S., et al., "Predictive Value of Prominent Pulmonary Arterial Wedge V Waves in Assessing the Presence and Severity of Mitral Regurgitation," Valvular Heart Disease, The American Journal of Cardiology, Mar. 15, 1994, vol. 73, No. 8, pp. 568-570.

Tice F.D., et al., "Transesophageal Echocardiographic Assessment of Reversal of Systolic Pulmonary Venous Flow in Mitral Stenosis," The American Journal of Cardiology, Jan. 1, 1995, vol. 75, No. 1, pp. 58-60.

* cited by examiner $A_1$ 65 67 70 69 60 88 99 97 93 71 PROXIMAL DISTAL 92 G 90 $S_1$ 75 94 96 $\theta_1$ 701 $P_f$ 98 91 $P_1$ 702 95 $D_1$ $S_2$ 88 $D_2$ 70
89
92
98
75
88
801
$\theta_2$
67
93
$A_1$
90
87
94
$D_1$
$D_2$ 70
98
75
88
60
93
90
95

FIG. 11A
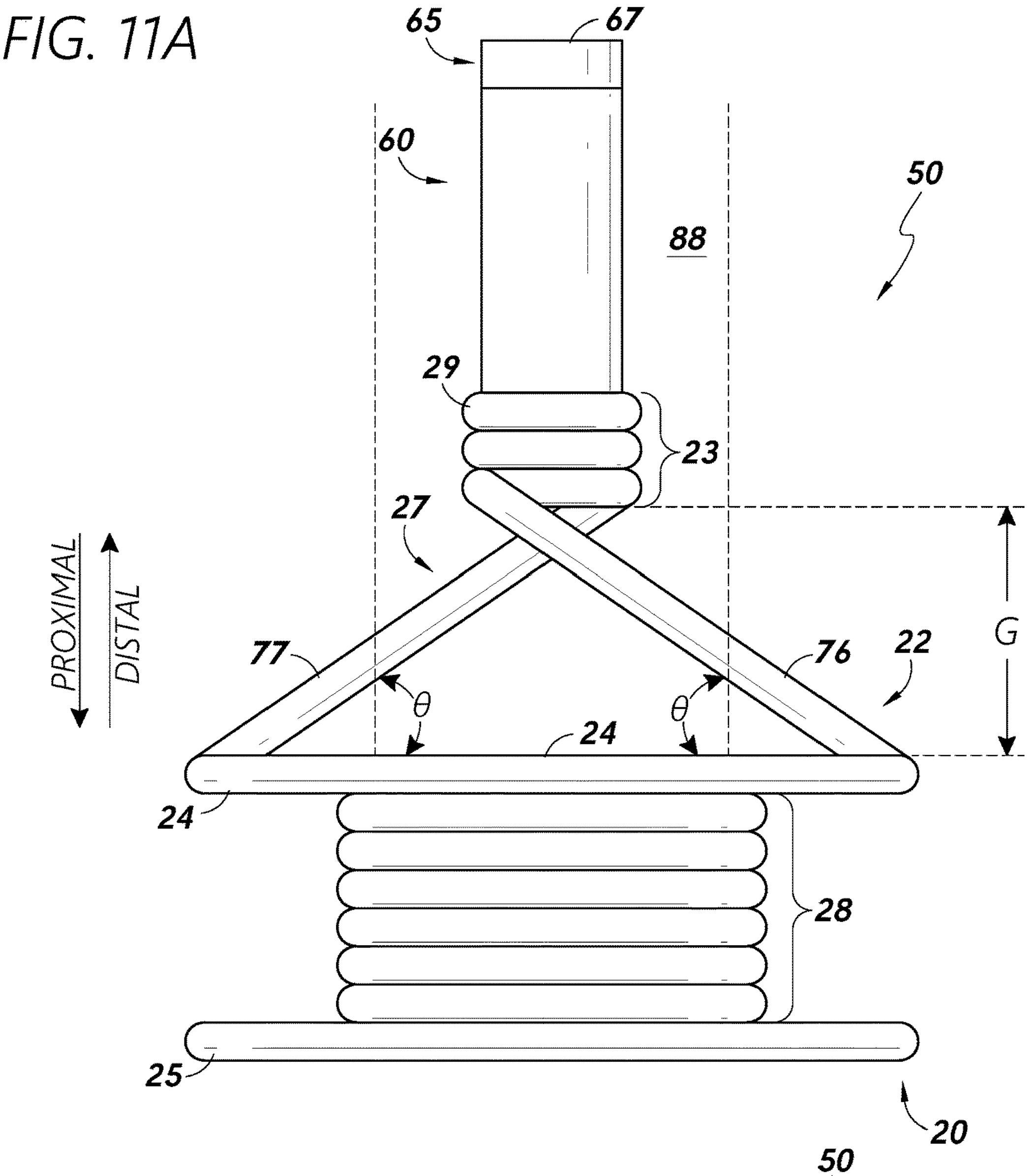
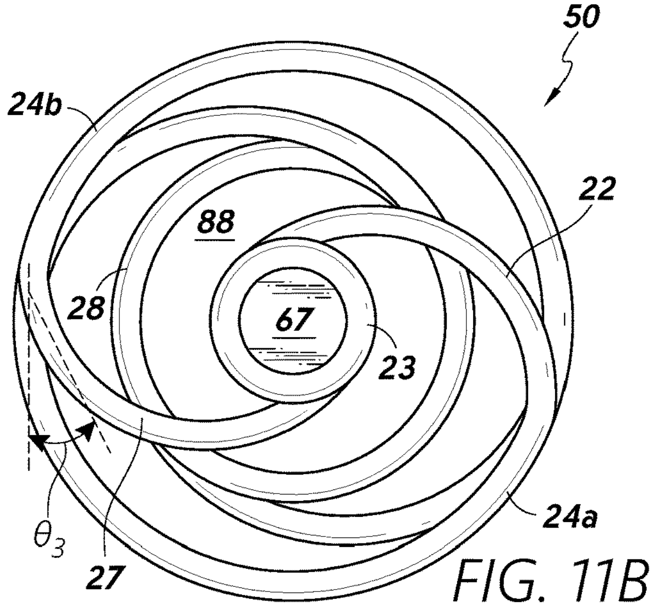
FIG. 11B

SHUNT IMPLANT DEVICES WITH OVER-CHANNEL SENSOR ARMS

RELATED APPLICATION

This application is a continuation of International Patent Application No. PCT/US2022/018748, filed Mar. 3, 2022, and entitled SHUNT IMPLANT DEVICES WITH OVER-CHANNEL SENSOR ARMS, which claims priority to U.S. Provisional Patent Application Ser. No. 63/161,385, filed Mar. 15, 2021 and entitled SHUNT IMPLANT DEVICES WITH OVER-CHANNEL SENSOR ARMS, the complete disclosure of which is hereby incorporated by reference in its entirety.

BACKGROUND

Field

The present disclosure generally relates to the field of medical implant devices.

Description of Related Art

Various medical procedures involve the implantation of a medical implant devices within the anatomy of the heart. Certain physiological parameters associated with such anatomy, such as fluid pressure, can have an impact on patient health prospects.

SUMMARY

Described herein are one or more methods and/or devices to facilitate monitoring of physiological parameter(s) associated with certain chambers and/or vessels of the heart, such as the left atrium, using one or more sensor implant devices.

In some implementations, the present disclosure relates to a sensor implant device comprising a shunt body that forms a fluid conduit, a first anchor structure associated with a first axial end of the shunt body, a second anchor structure associated with a second axial end of the shunt body, and a first sensor device coupled to the first anchor structure, the first anchor structure being configured to hold the first sensor device in a sensing position over a channel area of the fluid conduit.

In some embodiments, when in the sensing position, the first sensor device is aligned with an axis of the fluid conduit. For example, when in the sensing position, the first sensor device may be coaxial with the fluid conduit.

The first anchor structure can be wrapped around a body of the first sensor device.

The first anchor structure may comprise a first arm that extends from the shunt body over the channel area and holds the first sensor device. For example, the first anchor structure can further comprise a second arm that extends from the shunt body over the channel area and holds the first sensor device. In some embodiments, the first arm and the second arm emanate from opposite sides of the shunt body. For example, both the first arm and the second arm may wrap around a circumference of a body of the first sensor device.

In some embodiments, when the first sensor device is in held in the sensing position, an axial blood flow gap is present between the first sensor device and the first axial end of the shunt body.

In some embodiments, the shunt body comprises a helical wireform. For example, the first anchor structure may comprise a spiraled arm that is an integrated form with the helical wireform of the shunt body. In some embodiments, the shunt body further comprises a cover disposed outside at least a portion of the helical wireform.

The shunt body can further comprise a cover disposed within at least a portion of the helical wireform.

The sensor implant device can further comprise a second sensor device coupled to the second anchor structure, the second anchor structure being configured to hold the second sensor device over the channel area of the fluid conduit. For example, a sensor transducer of the first sensor device and a sensor transducer of the second sensor device may face in opposite directions. The first sensor device and the second sensor device are coaxial.

In some implementations, the present disclosure relates to a sensor implant device comprising a coil wireform. The coil wireform comprises, in a deployed configuration, a body portion formed of a plurality of winds of coil of the coil wireform and having a first diameter, a first flange anchor portion emanating from a first axial end of the body portion and having a second diameter that is greater than the first diameter, a first sensor-support arm emanating from the first flange portion and deflected radially over a channel area defined by the body portion, a distal portion of the first sensor-support arm including a sensor-retention means holding a first sensor device, and a second flange anchor portion emanating from a second axial end of the body portion.

The sensor implant device can further comprise a second sensor-support arm emanating from the second flange portion and deflected radially over the channel area.

In some embodiments, the sensor implant device further comprises a second sensor-support arm emanating from the first flange portion and deflected radially over the channel area, a distal portion of the second sensor-support arm being secured to the first sensor device.

In some embodiments, the first sensor-support arm is deflected axially with respect to an axis of the body portion at a greater angle than a deflection angle of the plurality of winds of coil of the body portion.

The sensor-retention means can comprise one or more winds of coil.

The sensor-retention means can comprise a mechanical clip.

The sensor implant device can further comprise a sealing means associated with the body portion. For example, the sealing means can comprise a fabric layer.

In some embodiments, the coil wireform comprises shape memory material configured to assume the deployed configuration when deployed from a delivery catheter. For example, the coil wireform can be configured to be compressed into a delivery configuration in which the body portion and the first flange anchor portion have a third diameter that is smaller than the first diameter.

For purposes of summarizing the disclosure, certain aspects, advantages, and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 7-1 illustrates a side view of a sensor implant device in accordance with one or more embodiments.

FIG. 7-2 illustrates a sensor assembly/device in accordance with one or more embodiments.

FIGS. 11A and 11B show side and axial views, respectively, of a sensor implant device having a dual-arm sensor holder in accordance with one or more embodiments.

FIGS. 17-1, 17-2, 17-3, 17-4, and 17-5 provide a flow diagram illustrating a process for implanting a sensor implant device in accordance with one or more embodiments.

FIGS. 18-1, 18-2, 18-3, 18-4, and 18-5 provide images of cardiac anatomy and certain devices/systems corresponding to operations of the process of FIGS. 17-1, 17-2, 17-3, 17-4, and 17-5 in accordance with one or more embodiments.

DETAILED DESCRIPTION

Figure 1:
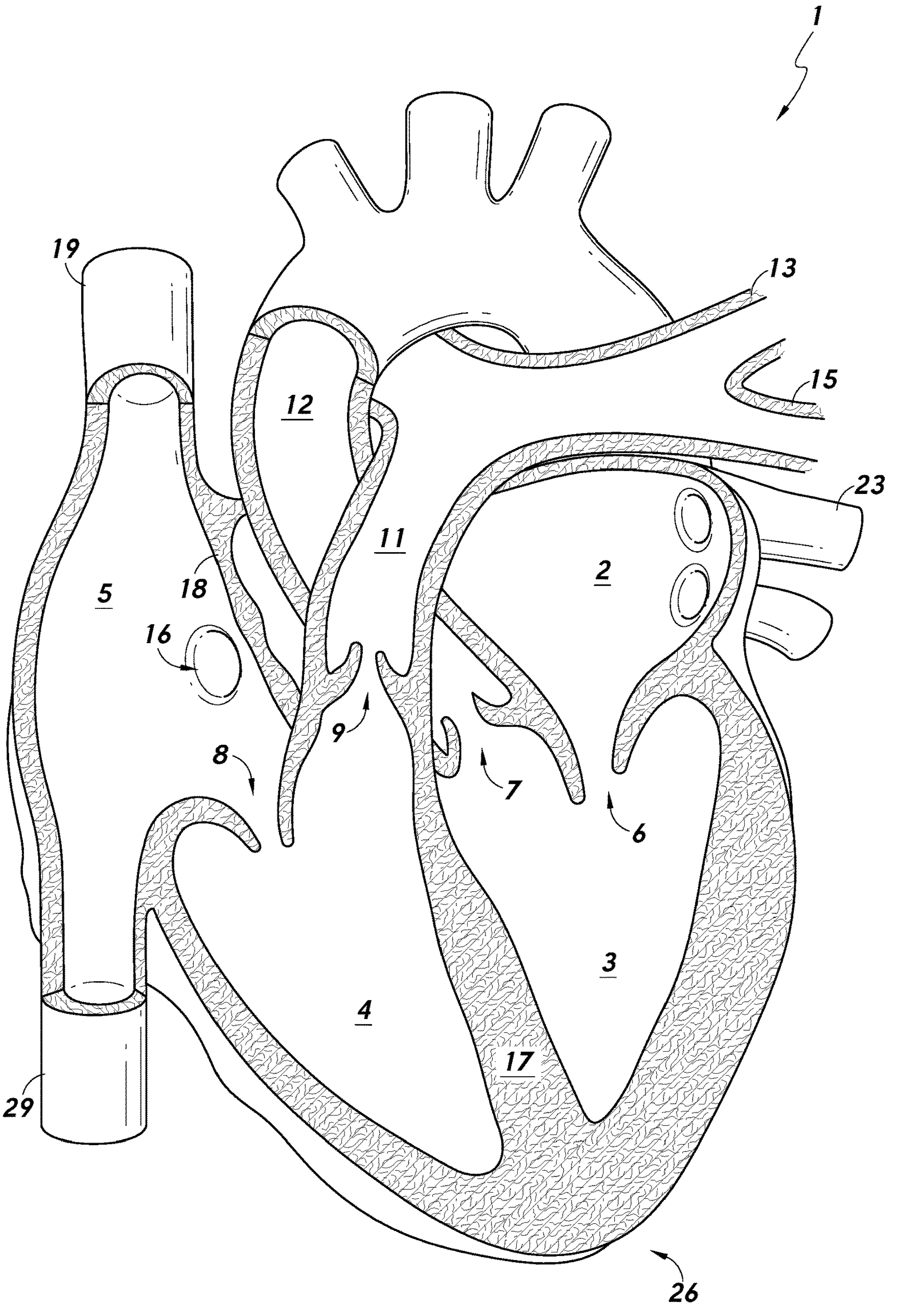
FIG. 1 illustrates an example representation of a human heart in accordance with one or more embodiments.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain reference numbers are re-used across different figures of the figure set of the present disclosure as a matter of convenience for devices, components, systems, features, and/or modules having features that may be similar in one or more respects. However, with respect to any of the embodiments disclosed herein, re-use of common reference numbers in the drawings does not necessarily indicate that such features, devices, components, or modules are identical or similar. Rather, one having ordinary skill in the art may be informed by context with respect to the degree to which usage of common reference numbers can imply similarity between referenced subject matter. Use of a particular reference number in the context of the description of a particular figure can be understood to relate to the identified device, component, aspect, feature, module, or system in that particular figure, and not necessarily to any devices, components, aspects, features, modules, or systems identified by the same reference number in another figure. Furthermore, aspects of separate figures identified with common reference numbers can be interpreted to share characteristics or to be entirely independent of one another.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

The present disclosure relates to systems, devices, and methods for monitoring of one or more physiological parameters of a patient (e.g., blood pressure) using sensor-integrated cardiac shunts and/or other medical implant devices. In some implementations, the present disclosure relates to cardiac shunts and/or other cardiac implant devices that incorporate or are associated with pressure sensors or other sensor devices. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly. Certain embodiments are disclosed herein in the context of cardiac implant devices. However, although certain principles disclosed herein are particularly applicable to the anatomy of the heart, it should be understood that sensor implant devices in accordance with the present disclosure may be implanted in, or configured for implantation in, any suitable or desirable anatomy.

Cardiac Physiology

The anatomy of the heart is described below to assist in the understanding of certain inventive concepts disclosed herein. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

Figure 2:
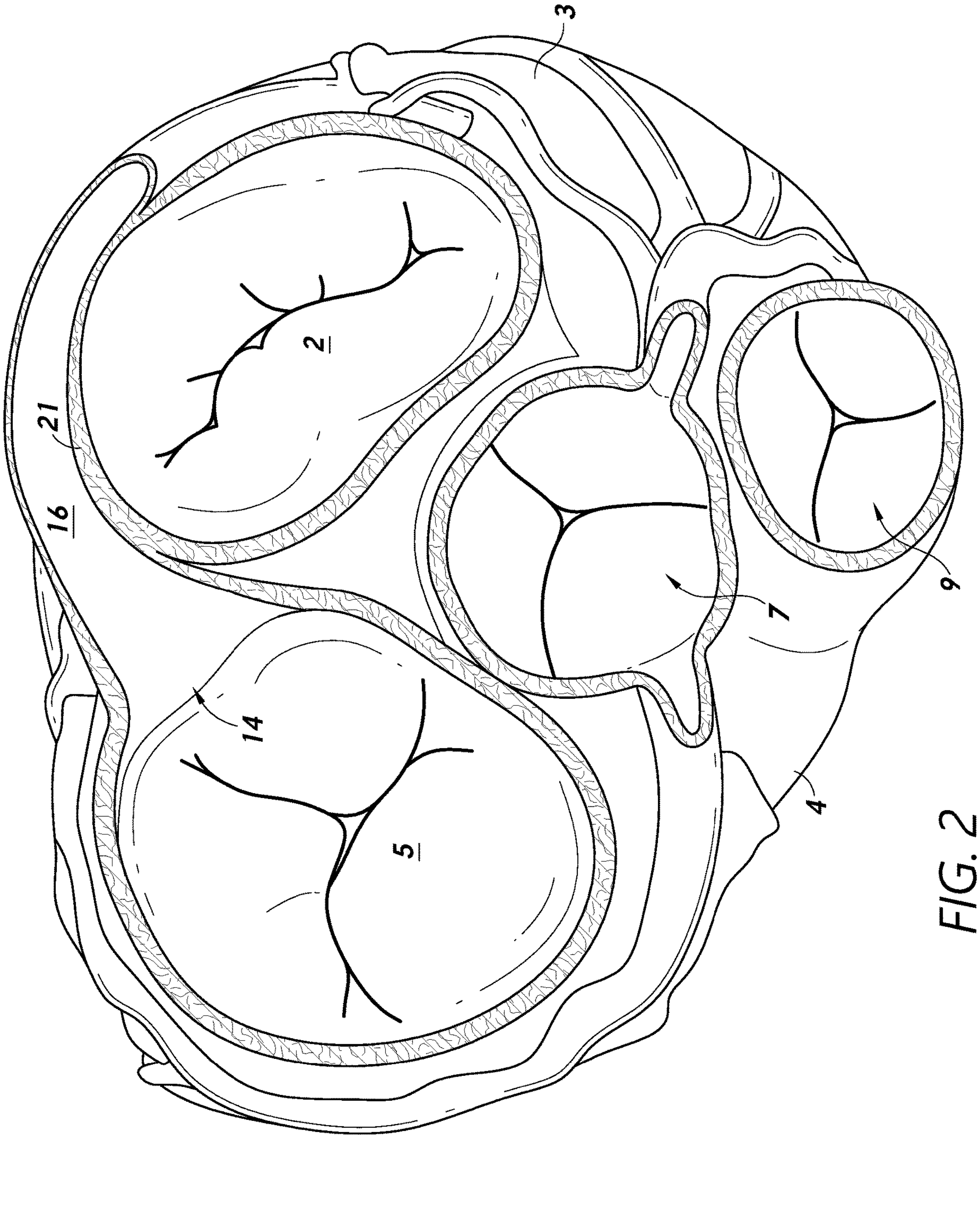
FIG. 2 illustrates a superior view of a human heart in accordance with one or more embodiments.

FIGS. 1 and 2 illustrate vertical/frontal and horizontal/superior cross-sectional views, respectively, of an example heart 1 having various features/anatomy relevant to certain aspects of the present inventive disclosure. The heart 1 includes four chambers, namely the left atrium 2, the left ventricle 3, the right ventricle 4, and the right atrium 5. In terms of blood flow, blood generally flows from the right ventricle 4 into the pulmonary artery 11 via the pulmonary valve 9, which separates the right ventricle 4 from the pulmonary artery 11 and is configured to open during systole so that blood may be pumped toward the lungs and close during diastole to prevent blood from leaking back into the heart from the pulmonary artery 11. The pulmonary artery 11 carries deoxygenated blood from the right side of the heart to the lungs.

In addition to the pulmonary valve 9, the heart 1 includes three additional valves for aiding the circulation of blood therein, including the tricuspid valve 8, the aortic valve 7, and the mitral valve 6. The tricuspid valve 8 separates the right atrium 5 from the right ventricle 4. The tricuspid valve 8 generally has three cusps or leaflets and may generally close during ventricular contraction (i.e., systole) and open during ventricular expansion (i.e., diastole). The mitral valve 6 generally has two cusps/leaflets and separates the left atrium 2 from the left ventricle 3. The mitral valve 6 is configured to open during diastole so that blood in the left atrium 2 can flow into the left ventricle 3, and, when functioning properly, closes during systole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage. Disfunction of a heart valve and/or associated leaflets (e.g., pulmonary valve disfunction) can result in valve leakage and/or other health complications.

The atrioventricular (i.e., mitral and tricuspid) heart valves may further comprise a collection of chordae tendineae and papillary muscles (not shown) for securing the leaflets of the respective valves to promote and/or facilitate proper coaptation of the valve leaflets and prevent prolapse thereof. The papillary muscles, for example, may generally comprise finger-like projections from the ventricle wall. The valve leaflets are connected to the papillary muscles by the chordae tendineae. A wall of muscle, referred to as the septum, separates the left-side chambers from the right-side chambers. In particular, an atrial septum wall portion 18 (referred to herein as the "atrial septum," "atrial septum," or "septum") separates the left atrium 2 from the right atrium 5, whereas a ventricular septum wall portion 17 (referred to herein as the "ventricular septum," "interventricular septum," or "septum") separates the left ventricle 3 from the right ventricle 4. The inferior tip 14 of the heart 1 is referred to as the apex and is generally located on or near the midclavicular line, in the fifth intercostal space.

The coronary sinus 16 comprises a collection of veins joined together to form a relatively large vessel that collects blood from the heart muscle (myocardium). The ostium of the coronary sinus 16, which can be guarded at least in part by a Thebesian valve in some patients, is open to the right atrium 5, as shown. The coronary sinus runs along a posterior aspect of the left atrium 2 and delivers less-oxygenated blood to the right atrium 5. The coronary sinus generally runs transversely in the left atrioventricular groove on the posterior side of the heart.

Health Conditions Associated with Cardiac Pressure and Other Parameters

As referenced above, certain physiological conditions or parameters associated with the cardiac anatomy can impact the health of a patient. For example, congestive heart failure is a condition associated with the relatively slow movement of blood through the heart and/or body, which causes the fluid pressure in one or more chambers of the heart to increase. As a result, the heart does not pump sufficient oxygen to meet the body's needs. The various chambers of the heart may respond to pressure increases by stretching to hold more blood to pump through the body or by becoming relatively stiff and/or thickened. The walls of the heart can eventually weaken and become unable to pump as efficiently. In some cases, the kidneys may respond to cardiac inefficiency by causing the body to retain fluid. Fluid build-up in arms, legs, ankles, feet, lungs, and/or other organs can cause the body to become congested, which is referred to as congestive heart failure. Acute decompensated congestive heart failure is a leading cause of morbidity and mortality, and therefore treatment and/or prevention of congestive heart failure is a significant concern in medical care.

The treatment and/or prevention of heart failure (e.g., congestive heart failure) can advantageously involve the monitoring of pressure in one or more chambers or regions of the heart or other anatomy. As described above, pressure buildup in one or more chambers or areas of the heart can be associated with congestive heart failure. Without direct or indirect monitoring of cardiac pressure, it can be difficult to infer, determine, or predict the presence or occurrence of congestive heart failure. For example, treatments or approaches not involving direct or indirect pressure monitoring may involve measuring or observing other present physiological conditions of the patient, such as measuring body weight, thoracic impedance, right heart catheterization, or the like. In some solutions, pulmonary capillary wedge pressure can be measured as a surrogate of left atrial pressure. For example, a pressure sensor may be disposed or implanted in the pulmonary artery, and readings associated therewith may be used as a surrogate for left atrial pressure. However, with respect to catheter-based pressure measurement in the pulmonary artery or certain other chambers or regions of the heart, use of invasive catheters may be required to maintain such pressure sensors, which may be uncomfortable or difficult to implement. Furthermore, certain lung-related conditions may affect pressure readings in the pulmonary artery, such that the correlation between pulmonary artery pressure and left atrial pressure may be undesirably attenuated. As an alternative to pulmonary artery pressure measurement, pressure measurements in the right ventricle outflow tract may relate to left atrial pressure as well. However, the correlation between such pressure readings and left atrial pressure may not be sufficiently strong to be utilized in congestive heart failure diagnostics, prevention, and/or treatment.

Additional solutions may be implemented for deriving or inferring left atrial pressure. For example, the E/A ratio, which is a marker of the function of the left ventricle of the heart representing the ratio of peak velocity blood flow from gravity in early diastole (the E wave) to peak velocity flow in late diastole caused by atrial contraction (the A wave), can be used as a surrogate for measuring left atrial pressure. The FJA ratio may be determined using echocardiography or other imaging technology; generally, abnormalities in the E/A ratio may suggest that the left ventricle cannot fill with blood properly in the period between contractions, which may lead to symptoms of heart failure, as explained above. However, E/A ratio determination generally does not provide absolute pressure measurement values.

Various methods for identifying and/or treating congestive heart failure involve the observation of worsening congestive heart failure symptoms and/or changes in body weight. However, such signs may appear relatively late and/or be relatively unreliable. For example, daily body-weight measurements may vary significantly (e.g., up to 9% or more) and may be unreliable in signaling heart-related complications. Furthermore, treatments guided by monitoring signs, symptoms, weight, and/or other biomarkers have not been shown to substantially improve clinical outcomes. In addition, for patients that have been discharged, such treatments may necessitate remote telemedicine systems.

The present disclosure provides systems, devices, and methods for guiding the administration of medication relating to the treatment of congestive heart failure at least in part by directly monitoring pressure in the left atrium, or other chamber or vessel for which pressure measurements are indicative of left atrial pressure and/or pressure levels in one or more other vessels/chambers, such as for congestive heart failure patients in order to reduce hospital readmissions, morbidity, and/or otherwise improve the health prospects of the patient.

Cardiac Pressure Monitoring

Cardiac pressure monitoring in accordance with embodiments of the present disclosure may provide a proactive intervention mechanism for preventing or treating congestive heart failure and/or other physiological conditions. Generally, increases in ventricular filling pressures associated with diastolic and/or systolic heart failure can occur prior to the occurrence of symptoms that lead to hospitalization. For example, cardiac pressure indicators may present weeks prior to hospitalization with respect to some patients. Therefore, pressure monitoring systems in accordance with embodiments of the present disclosure may advantageously be implemented to reduce instances of hospitalization by guiding the appropriate or desired titration and/or administration of medications before the onset of heart failure.

Dyspnea represents a cardiac pressure indicator characterized by shortness of breath or the feeling that one cannot breathe sufficiently. Dyspnea may result from elevated atrial pressure, which may cause fluid buildup in the lungs from pressure back-up. Pathological dyspnea can result from congestive heart failure. However, a significant amount of time may elapse between the time of initial pressure elevation and the onset of dyspnea, and therefore symptoms of dyspnea may not provide sufficiently-early signaling of elevated atrial pressure. By monitoring pressure directly according to embodiments of the present disclosure, normal ventricular filling pressures may advantageously be maintained, thereby preventing or reducing effects of heart failure, such as dyspnea.

Figure 3:
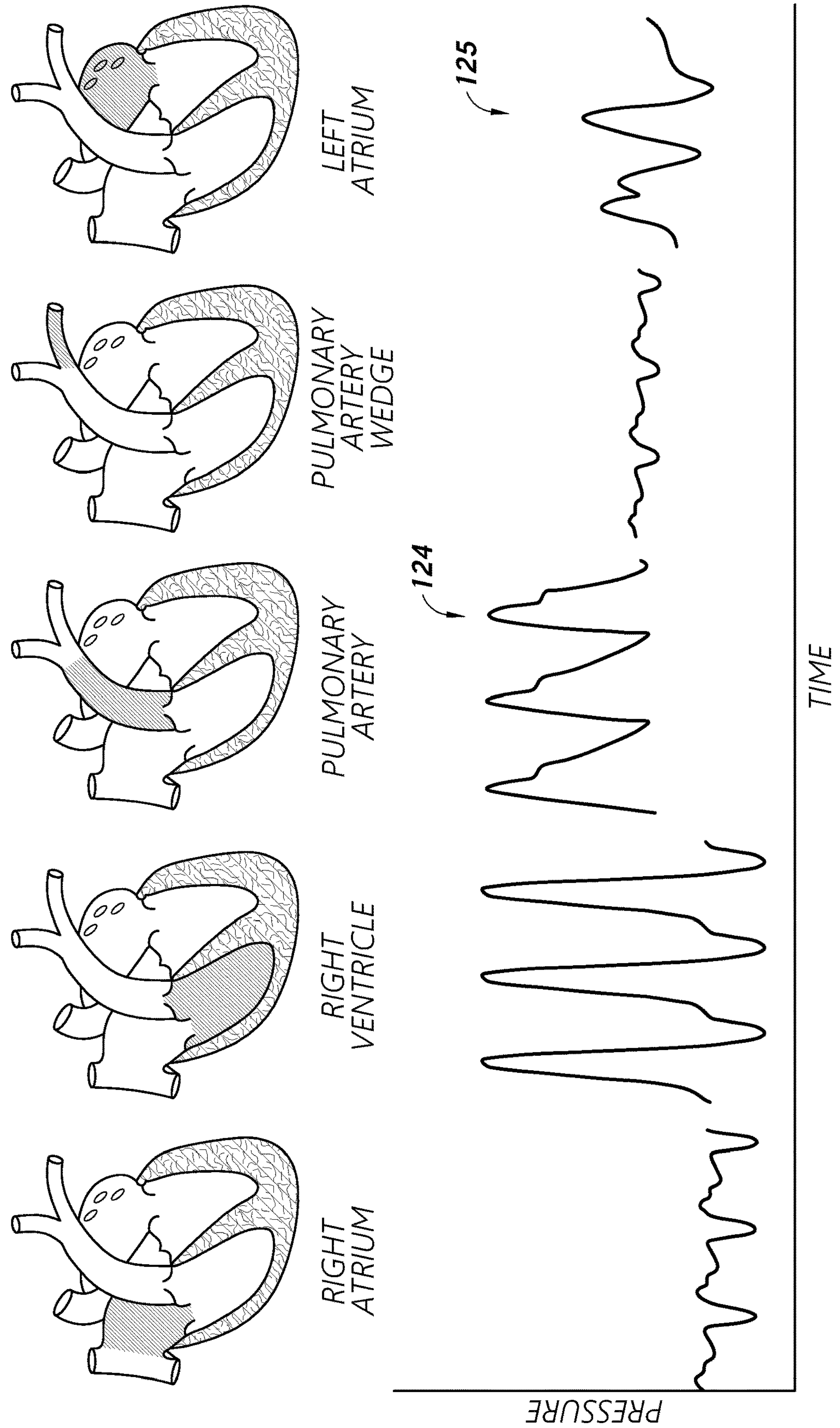
FIG. 3 illustrates example pressure waveforms associated with various chambers and vessels of the heart according to one or more embodiments.

As referenced above, with respect to cardiac pressures, pressure elevation in the left atrium may be particularly correlated with heart failure. FIG. 3 illustrates example pressure waveforms associated with various chambers and vessels of the heart according to one or more embodiments. The various waveforms illustrated in FIG. 3 may represent waveforms obtained using right heart catheterization to advance one or more pressure sensors to the respective illustrated and labeled chambers or vessels of the heart. As illustrated in FIG. 3, the waveform 125, which represents left atrial pressure, may be considered to provide the best feedback for early detection of congestive heart failure. Furthermore, there may generally be a relatively strong correlation between increases and left atrial pressure and pulmonary congestion.

Left atrial pressure may generally correlate well with left ventricular end-diastolic pressure. However, although left atrial pressure and end-diastolic pulmonary artery pressure can have a significant correlation, such correlation may be weakened when the pulmonary vascular resistance becomes elevated. That is, pulmonary artery pressure generally fails to correlate adequately with left ventricular end-diastolic pressure in the presence of a variety of acute conditions, which may include certain patients with congestive heart failure. For example, pulmonary hypertension, which affects approximately 25% to 83% of patients with heart failure, can affect the reliability of pulmonary artery pressure measurement for estimating left-sided filling pressure. Therefore, pulmonary artery pressure measurement alone, as represented by the waveform 124, may be an insufficient or inaccurate indicator of left ventricular end-diastolic pressure, particularly for patients with comorbidities, such as lung disease and/or thromboembolism. Left atrial pressure may further be correlated at least partially with the presence and/or degree of mitral regurgitation.

Left atrial pressure readings may be relatively less likely to be distorted or affected by other conditions, such as respiratory conditions or the like, compared to the other pressure waveforms shown in FIG. 3. Generally, left atrial pressure may be significantly predictive of heart failure, such as up two weeks before manifestation of heart failure. For example, increases in left atrial pressure, and both diastolic and systolic heart failure, may occur weeks prior to hospitalization, and therefore knowledge of such increases may be used to predict the onset of congestive heart failure, such as acute debilitating symptoms of congestive heart failure.

Cardiac pressure monitoring, such as left atrial pressure monitoring, can provide a mechanism to guide administration of medication to treat and/or prevent congestive heart failure. Such treatments may advantageously reduce hospital readmissions and morbidity, as well as provide other benefits. An implanted pressure sensor in accordance with embodiments of the present disclosure may be used to predict heart failure up two weeks or more before the manifestation of symptoms or markers of heart failure (e.g., dyspnea). When heart failure predictors are recognized using cardiac pressure sensor embodiments in accordance with the present disclosure, certain prophylactic measures may be implemented, including medication intervention, such as modification to a patient's medication regimen, which may help prevent or reduce the effects of cardiac dysfunction. Direct pressure measurement in the left atrium can advantageously provide an accurate indicator of pressure buildup that may lead to heart failure or other complications. For example, trends of atrial pressure elevation may be analyzed or used to determine or predict the onset of cardiac dysfunction, wherein drug or other therapy may be augmented to cause reduction in pressure and prevent or reduce further complications.

Figure 4:
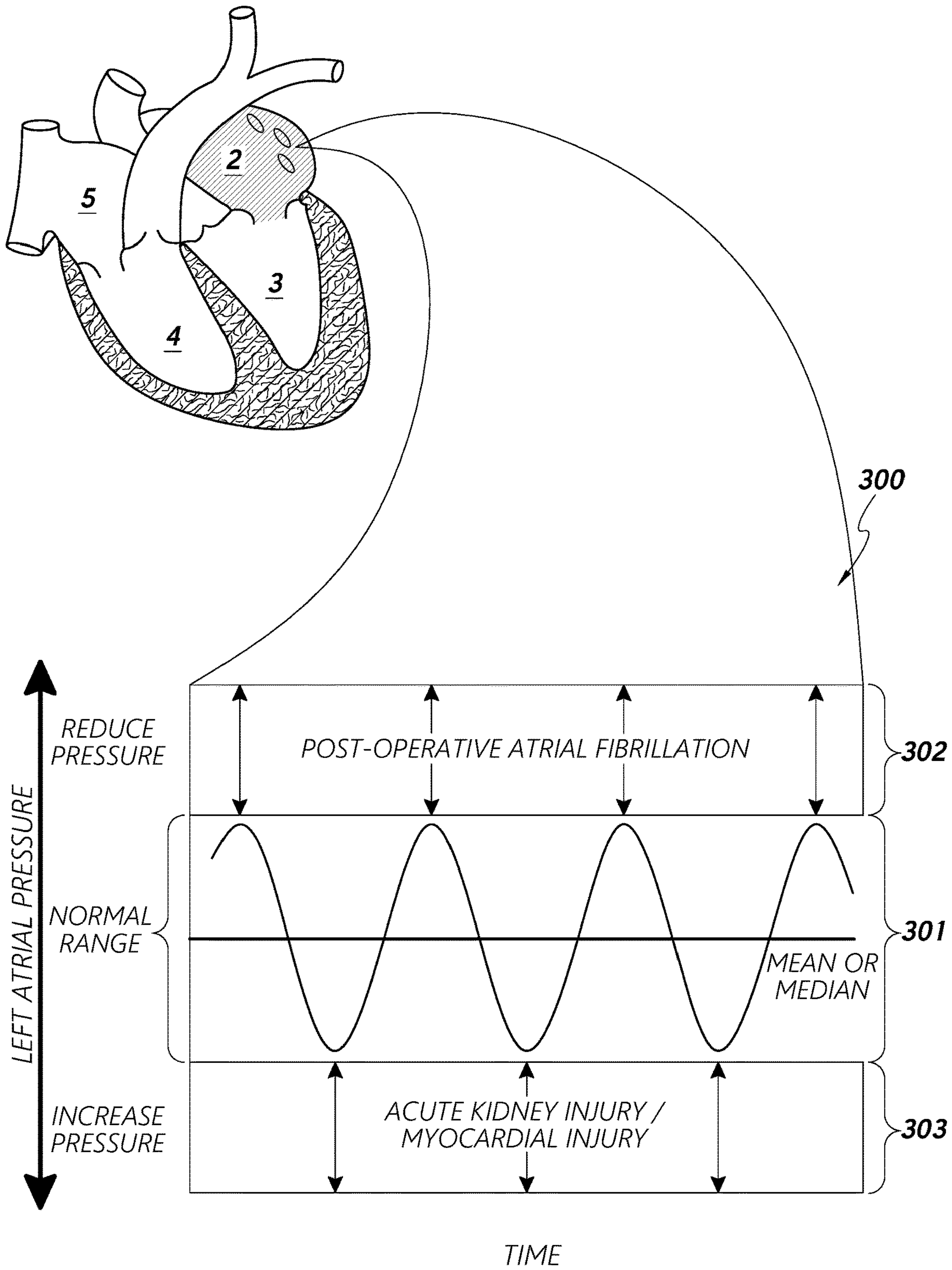
FIG. 4 illustrates a graph showing left atrial pressure ranges.

FIG. 4 illustrates a graph 300 showing left atrial pressure ranges including a normal range 301 of left atrial pressure that is not generally associated with substantial risk of postoperative atrial fibrillation, acute kidney injury, myocardial injury, heart failure and/or other health conditions. Embodiments of the present disclosure provide systems, devices, and methods for determining whether a patient's left atrial pressure is within the normal range 301, above the normal range 303, or below the normal range 302 through the use of certain sensor implant devices. For detected left atrial pressure above the normal range, which may be correlated with an increased risk of heart failure, embodiments of the present disclosure as described in detail below can inform efforts to reduce the left atrial pressure until it is brought within the normal range 301. Furthermore, for detected left atrial pressure that is below the normal range 301, which may be correlated with increased risks of acute kidney injury, myocardial injury, and/or other health complications, embodiments of the present disclosure as described in detail below can serve to facilitate efforts to increase the left atrial pressure to bring the pressure level within the normal range 301.

Sensor Implant Devices

Figure 5:
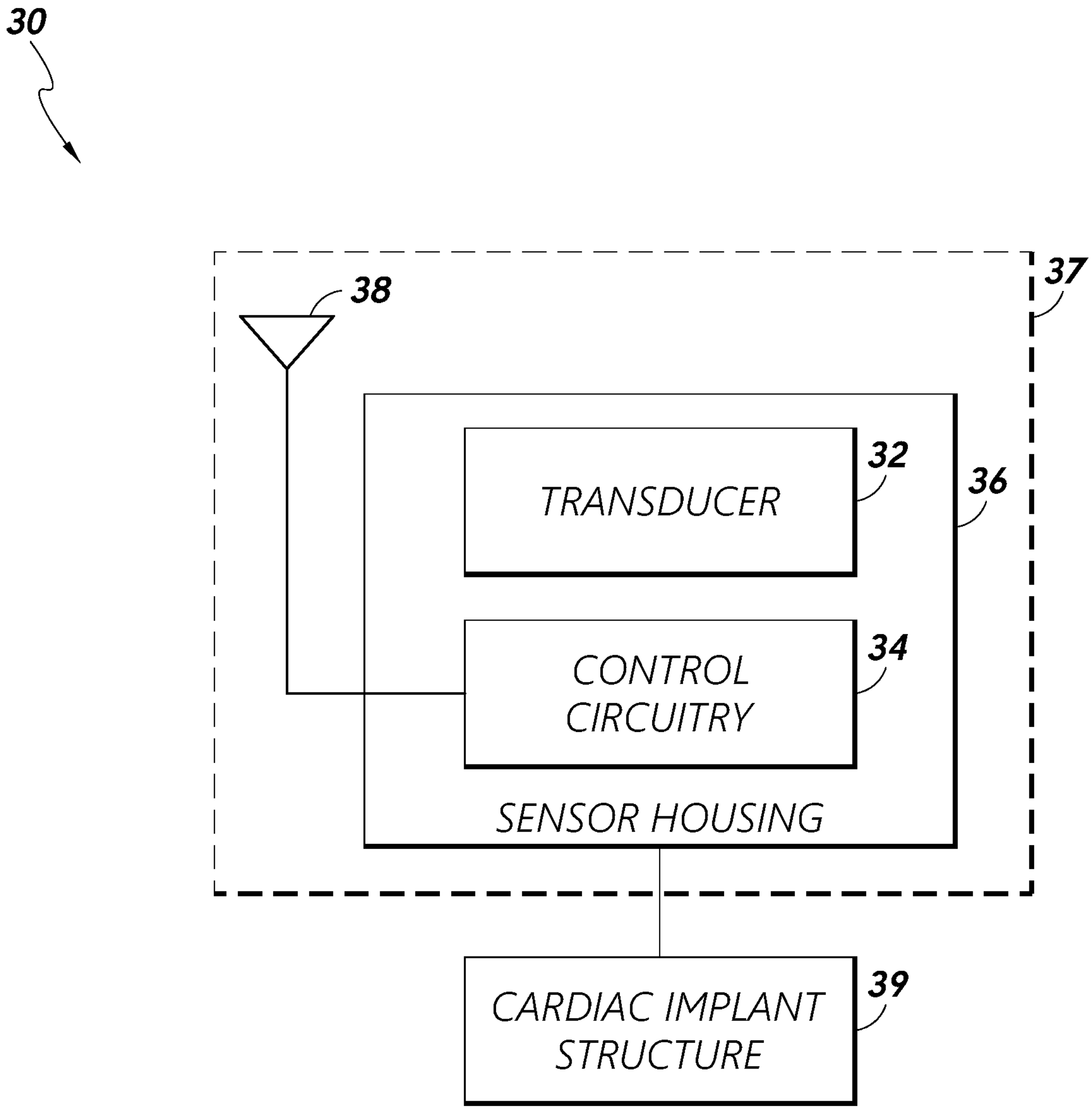
FIG. 5 is a block diagram representing a sensor implant device in accordance with one or more embodiments.

In some implementations, the present disclosure relates to sensors associated or integrated with cardiac shunts or other implant devices. Such integrated devices may be used to provide controlled and/or more effective therapies for treating and preventing heart failure and/or other health complications related to cardiac function. FIG. 5 is a block diagram illustrating an implant device 30 comprising a shunt (or other type of implant) structure 39. In some embodiments, the shunt structure 39 is physically integrated with and/or connected to a sensor device 37. The sensor device 37 may be, for example, a pressure sensor, or other type of sensor. In some embodiments, the sensor 37 comprises a transducer 32, such as a pressure transducer, as well as certain control circuitry 34, which may be embodied in, for example, an application-specific integrated circuit (ASIC).

The control circuitry 34 may be configured to process signals received from the transducer 32 and/or communicate signals associated therewith wirelessly through biological tissue using the antenna 38. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, microcontrollers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further comprise one or more, storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry. The transducer(s) 32 and/or antenna(s) 38 can be considered part of the control circuitry 34.

The antenna 38 may comprise one or more coils or loops of conductive material, such as copper wire or the like. In some embodiments, at least a portion of the transducer 32, control circuitry 34, and/or the antenna 38 are at least partially disposed or contained within a sensor housing 36, which may comprise any type of material, and may advantageously be at least partially hermetically sealed. For example, the housing 36 may comprise glass or other rigid material in some embodiments, which may provide mechanical stability and/or protection for the components housed therein. In some embodiments, the housing 36 is at least partially flexible. For example, the housing may comprise polymer or other flexible structure/material, which may advantageously allow for folding, bending, or collapsing of the sensor 37 to allow for transportation thereof through a catheter or other introducing means.

The transducer 32 may comprise any type of sensor means or mechanism. For example, the transducer 32 may be a force-collector-type pressure sensor. In some embodiments, the transducer 32 comprises a diaphragm, piston, bourdon tube, bellows, or other strain- or deflection-measuring component(s) to measure strain or deflection applied over an area/surface thereof. The transducer 32 may be associated with the housing 36, such that at least a portion thereof is contained within or attached to the housing 36.

With respect to sensor devices/components being "associated with" a stent or other implant structure, such terminology may refer to a sensor device or component being physically coupled, attached, or connected to, or integrated with, the implant structure.

In some embodiments, the transducer 32 comprises or is a component of a piezoresistive strain gauge, which may be configured to use a bonded or formed strain gauge to detect strain due to applied pressure, wherein resistance increases as pressure deforms the component/material. The transducer 32 may incorporate any type of material, including but not limited to silicon (e.g., monocrystalline), polysilicon thin film, bonded metal foil, thick film, silicon-on-sapphire, sputtered thin film, and/or the like.

In some embodiments, the transducer 32 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicon, and the like. In some embodiments, the transducer 32 comprises or is a component of an electromagnetic pressure sensor, which may be configured to measure the displacement of a diaphragm by means of changes in inductance, linear variable displacement transducer (LVDT) functionality, Hall Effect, or eddy current sensing. In some embodiments, the transducer 32 comprises or is a component of a piezoelectric strain sensor. For example, such a sensor may determine strain (e.g., pressure) on a sensing mechanism based on the piezoelectric effect in certain materials, such as quartz.

In some embodiments, the transducer 32 comprises or is a component of a strain gauge. For example, a strain gauge embodiment may comprise a pressure sensitive element on or associated with an exposed surface of the transducer 32. In some embodiments, a metal strain gauge is adhered to a surface of the sensor, or a thin-film gauge may be applied on the sensor by sputtering or other technique. The measuring element or mechanism may comprise a diaphragm or metal foil. The transducer 32 may comprise any other type of sensor or pressure sensor, such as optical, potentiometric, resonant, thermal, ionization, or other types of strain or pressure sensors.

Figure 6:
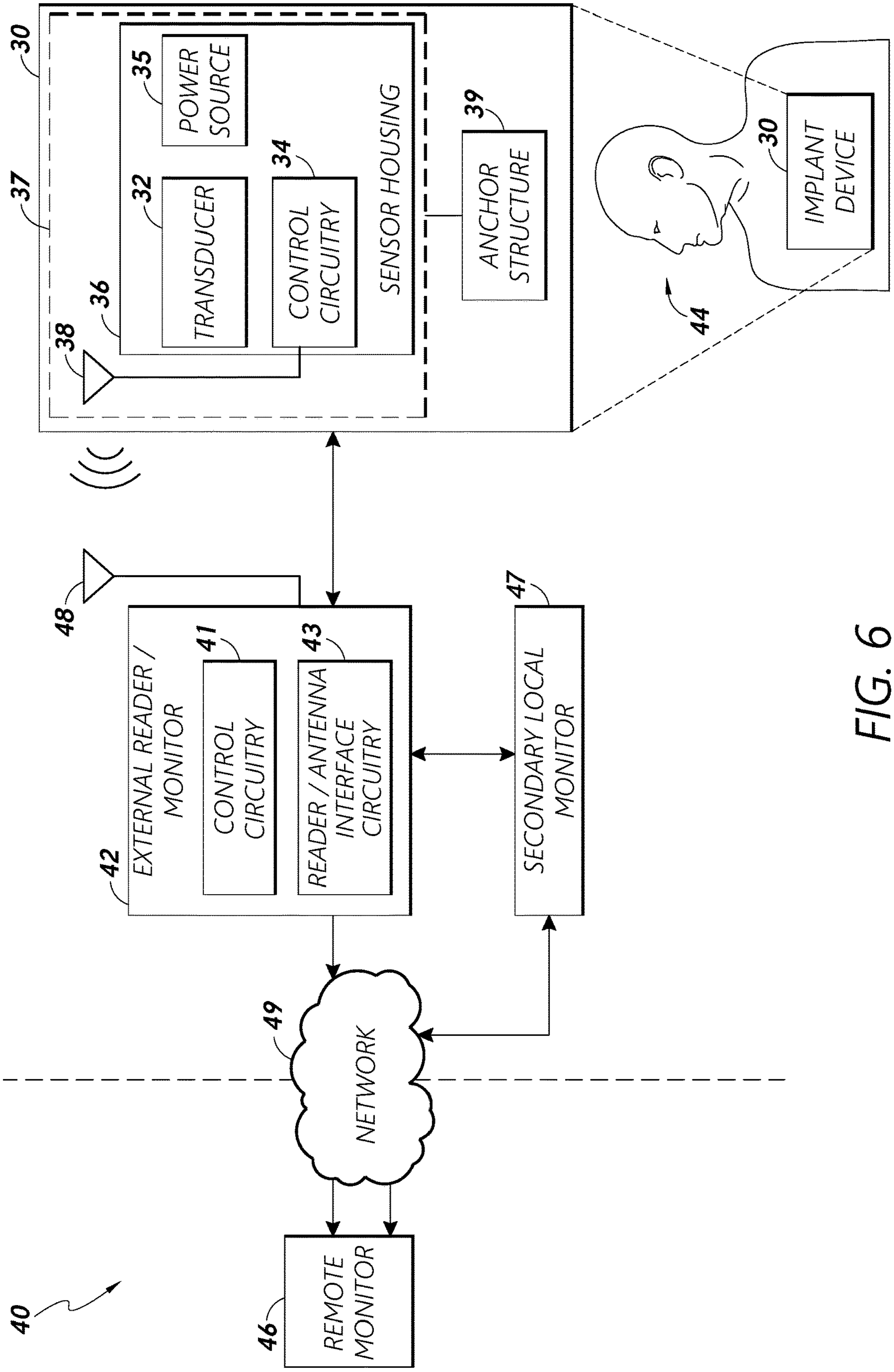
FIG. 6 is a block diagram representing a system for monitoring one or more physiological parameters associated with a patient according to one or more embodiments.

FIG. 6 shows a system 40 for monitoring one or more physiological parameters (e.g., left atrial pressure and/or volume) in a patient 44 according to one or more embodiments. The patient 44 can have a medical implant device 30 implanted in, for example, the heart (not shown), or associated physiology, of the patient 44. For example, the implant device 30 can be implanted at least partially within the left atrium and/or coronary sinus of the patient's heart. The implant device 30 can include one or more sensor transducers 32, such as one or more microelectromechanical system (MEMS) devices (e.g., MEMS pressure sensors, or other type of sensor transducer).

In certain embodiments, the monitoring system 40 can comprise at least two subsystems, including an implantable internal subsystem or device 30 that includes the sensor transducer(s) 32, as well as control circuitry 34 comprising one or more microcontroller(s), discrete electronic component(s), and one or more power and/or data transmitter(s) 38 (e.g., antennae coil). The monitoring system 40 can further include an external (e.g., non-implantable) subsystem that includes an external reader 42 (e.g., coil), which may include a wireless transceiver that is electrically and/or communicatively coupled to certain control circuitry 41. In certain embodiments, both the internal 30 and external 42 subsystems include a corresponding coil antenna for wireless communication and/or power delivery through patient tissue disposed therebetween. The sensor implant device 30 can be any type of implant device. For example, in some embodiments, the implant device 30 comprises a pressure sensor integrated with another functional implant structure 39, such as a prosthetic shunt or stent device/structure.

Certain details of the implant device 30 are illustrated in the enlarged block 30 shown. The implant device 30 can comprise an implant/anchor structure 39 as described herein. For example, the implant/anchor structure 39 can include a percutaneously-deliverable shunt device configured to be secured to and/or in a tissue wall to provide a flow path between two chambers and/or vessels of the heart, as described in detail throughout the present disclosure. The implant/anchor structure 39 can comprise a helical/coiled wireform in some embodiments, as disclosed in detail herein.

Although certain components are illustrated in FIG. 6 as part of the implant device 30, it should be understood that the sensor implant device 30 may only comprise a subset of the illustrated components/modules and can comprise additional components/modules not illustrated. The implant device may represent an embodiment of the implant device shown in FIG. 5, and vice versa. The implant device 30 can advantageously include one or more sensor transducers 32, which can be configured to provide a response indicative of one or more physiological parameters of the patient 44, such as atrial pressure. Although pressure transducers are described, the sensor transducer(s) 32 can comprise any suitable or desirable types of sensor transducer(s) for providing signals relating to physiological parameters or conditions associated with the implant device 30 and/or patient 44.

The sensor transducer(s) 32 can comprise one or more MEMS sensors, optical sensors, piezoelectric sensors, electromagnetic sensors, strain sensors/gauges, accelerometers, gyroscopes, diaphragm-based sensors, and/or other types of sensors, which can be positioned in the patient 44 to sense one or more parameters relevant to the health of the patient. The transducer 32 may be a force-collector-type pressure sensor. In some embodiments, the transducer 32 comprises a diaphragm, piston, bourdon tube, bellows, or other strain- or deflection-measuring component(s) to measure strain or deflection applied over an area/surface thereof. The transducer 32 may be associated with the sensor housing 36, such that at least a portion thereof is contained within, or attached to, the housing 36.

In some embodiments, the transducer 32 comprises or is a component of a strain gauge, which may be configured to use a bonded or formed strain gauge to detect strain due to applied pressure. For example, the transducer 32 may comprise or be a component of a piezoresistive strain gauge, wherein resistance increases as pressure deforms the component/material of the strain gauge. The transducer 32 may incorporate any type of material, including but not limited to silicone, polymer, silicon (e.g., monocrystalline), polysilicon thin film, bonded metal foil, thick film, silicon-on-sapphire, sputtered thin film, and/or the like. In some embodiments, a metal strain gauge is adhered to the sensor surface, or a thin-film gauge may be applied on the sensor by sputtering or other technique. The measuring element or mechanism may comprise a diaphragm or metal foil. The transducer 32 may comprise any other type of sensor or pressure sensor, such as optical, potentiometric, resonant, thermal, ionization, or other types of strain or pressure sensors.

In some embodiments, the transducer 32 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicone, silicon or other semiconductor, and the like. In some embodiments, the transducer 32 comprises or is a component of an electromagnetic pressure sensor, which may be configured to measures the displacement of a diaphragm by means of changes in inductance, linear variable displacement transducer (LVDT) functionality, Hall Effect, or eddy current sensing. In some embodiments, the transducer 32 comprises or is a component of a piezoelectric strain sensor. For example, such a sensor may determine strain (e.g., pressure) on a sensing mechanism based on the piezoelectric effect in certain materials, such as quartz.

In some embodiments, the transducer(s) 32 is/are electrically and/or communicatively coupled to the control circuitry 34, which may comprise one or more application-specific integrated circuit (ASIC) microcontrollers or chips. The control circuitry 34 can further include one or more discrete electronic components, such as tuning capacitors, resistors, diodes, inductors, or the like.

In certain embodiments, the sensor transducer(s) 32 can be configured to generate electrical signals that can be wirelessly transmitted to a device outside the patient's body, such as the illustrated local external monitor system 42. In order to perform such wireless data transmission, the implant device 30 can include radio frequency (RF) (or other frequency band) transmission circuitry, such as signal processing circuitry and an antenna 38. The antenna 38 can comprise an antenna coil implanted within the patient. The control circuitry 34 may comprise any type of transceiver circuitry configured to transmit an electromagnetic signal, wherein the signal can be radiated by the antenna 38, which may comprise one or more conductive wires, coils, plates, or the like. The control circuitry 34 of the implant device 30 can comprise, for example, one or more chips or dies configured to perform some amount of processing on signals generated and/or transmitted using the device 30. However, due to size, cost, and/or other constraints, the implant device 30 may not include independent processing capability in some embodiments.

The wireless signals generated by the implant device 30 can be received by the local external monitor device or subsystem 42, which can include a reader/antenna-interface circuitry module 43 configured to receive the wireless signal transmissions from the implant device 30, which is disposed at least partially within the patient 44. For example, the module 43 may include transceiver device(s)/circuitry.

The external local monitor 42 can receive the wireless signal transmissions from the implant device 30 and/or provide wireless power to the implant device 30 using an external antenna 48, such as a wand device. The reader/antenna-interface circuitry 43 can include radio-frequency (RF) (or other frequency band) front-end circuitry configured to receive and amplify the signals from the implant device 30, wherein such circuitry can include one or more filters (e.g., band-pass filters), amplifiers (e.g., low-noise amplifiers), analog-to-digital converters (ADC) and/or digital control interface circuitry, phase-locked loop (PLL) circuitry, signal mixers, or the like. The reader/antenna-interface circuitry 43 can further be configured to transmit signals over a network 49 to a remote monitor subsystem or device 46. The RF circuitry of the reader/antenna-interface circuitry 43 can further include one or more of digital-to-analog converter (DAC) circuitry, power amplifiers, low-pass filters, antenna switch modules, antennas or the like for treatment/processing of transmitted signals over the network 49 and/or for receiving signals from the implant device 30. In certain embodiments, the local monitor 42 includes control circuitry 41 for performing processing of the signals received from the implant device 30. The local monitor 42 can be configured to communicate with the network 49 according to a known network protocol, such as Ethernet. Wi-Fi, or the like. In certain embodiments, the local monitor 42 comprises a smartphone, laptop computer, or other mobile computing device, or any other type of computing device.

In certain embodiments, the implant device 30 includes some amount of volatile and/or non-volatile data storage. For example, such data storage can comprise solid-state memory utilizing an array of floating-gate transistors, or the like. The control circuitry 34 may utilize data storage for storing sensed data collected over a period of time, wherein the stored data can be transmitted periodically to the local monitor 42 or another external subsystem. In certain embodiments, the implant device 30 does not include any data storage. The control circuitry 34 may be configured to facilitate wireless transmission of data generated by the sensor transducer(s) 32, or other data associated therewith. The control circuitry 34 may further be configured to receive input from one or more external subsystems, such as from the local monitor 42, or from a remote monitor 46 over, for example, the network 49. For example, the implant device 30 may be configured to receive signals that at least partially control the operation of the implant device 30, such as by activating/deactivating one or more components or sensors, or otherwise affecting operation or performance of the implant device 30.

The one or more components of the implant device 30 can be powered by one or more power sources 35. Due to size, cost and/or electrical complexity concerns, it may be desirable for the power source 35 to be relatively minimalistic in nature. For example, high-power driving voltages and/or currents in the implant device 30 may adversely affect or interfere with operation of the heart or other body part associated with the implant device. In certain embodiments, the power source 35 is at least partially passive in nature, such that power can be received from an external source wirelessly by passive circuitry of the implant device 30, such as through the use of short-range, or near-field wireless power transmission, or other electromagnetic coupling mechanism. For example, the local monitor 42 may serve as an initiator that actively generates an RF field that can provide power to the implant device 30, thereby allowing the power circuitry of the implant device to take a relatively simple form factor. In certain embodiments, the power source 35 can be configured to harvest energy from environmental sources, such as fluid flow, motion, or the like. Additionally or alternatively, the power source 35 can comprise a battery, which can advantageously be configured to provide enough power as needed over the monitoring period (e.g., 3, 5, 10, 20, 30, 40, or 90 days, or other period of time).

In some embodiments, the local monitor device 42 can serve as an intermediate communication device between the implant device 30 and the remote monitor 46. The local monitor device 42 can be a dedicated external unit designed to communicate with the implant device 30. For example, the local monitor device 42 can be a wearable communication device, or other device that can be readily disposed in proximity to the patient 44 and implant device 30. The local monitor device 42 can be configured to continuously, periodically, or sporadically interrogate the implant device 30 in order to extract or request sensor-based information therefrom. In certain embodiments, the local monitor 42 comprises a user interface, wherein a user can utilize the interface to view sensor data, request sensor data, or otherwise interact with the local monitor system 42 and/or implant device 30.

The system 40 can include a secondary local monitor 47, which can be, for example, a desktop computer or other computing device configured to provide a monitoring station or interface for viewing and/or interacting with the monitored cardiac pressure data. In an embodiment, the local monitor 42 can be a wearable device or other device or system configured to be disposed in close physical proximity to the patient and/or implant device 30, wherein the local monitor 42 is primarily designed to receive/transmit signals to and/or from the implant device 30 and provide such signals to the secondary local monitor 47 for viewing, processing, and/or manipulation thereof. The external local monitor system 42 can be configured to receive and/or process certain metadata from or associated with the implant device 30, such as device ID or the like, which can also be provided over the data coupling from the implant device 30.

The remote monitor subsystem 46 can be any type of computing device or collection of computing devices configured to receive, process and/or present monitor data received over the network 49 from the local monitor device 42, secondary local monitor 47, and/or implant device 30. For example, the remote monitor subsystem 46 can advantageously be operated and/or controlled by a healthcare entity, such as a hospital, doctor, or other care entity associated with the patient 44. Although certain embodiments disclosed herein describe communication with the remote monitor subsystem 46 from the implant device indirectly through the local monitor device 42, in certain embodiments, the implant device 30 can comprise a transmitter capable of communicating over the network 49 with the remote monitor subsystem 46 without the necessity of relaying information through the local monitor device 42.

In some embodiments, at least a portion of the transducer 32, control circuitry 34, power source 35 and/or the antenna 38 are at least partially disposed or contained within the sensor housing 36, which may comprise any type of material, and may advantageously be at least partially hermetically sealed. For example, the housing 36 may comprise glass or other rigid material in some embodiments, which may provide mechanical stability and/or protection for the components housed therein. In some embodiments, the housing 36 is at least partially flexible. For example, the housing may comprise polymer or other flexible structure/material, which may advantageously allow for folding, bending, or collapsing of the sensor 30 to allow for transportation thereof through a catheter or other percutaneous introducing means.

Cardiac Shunt Implants

Figures 1, 7:
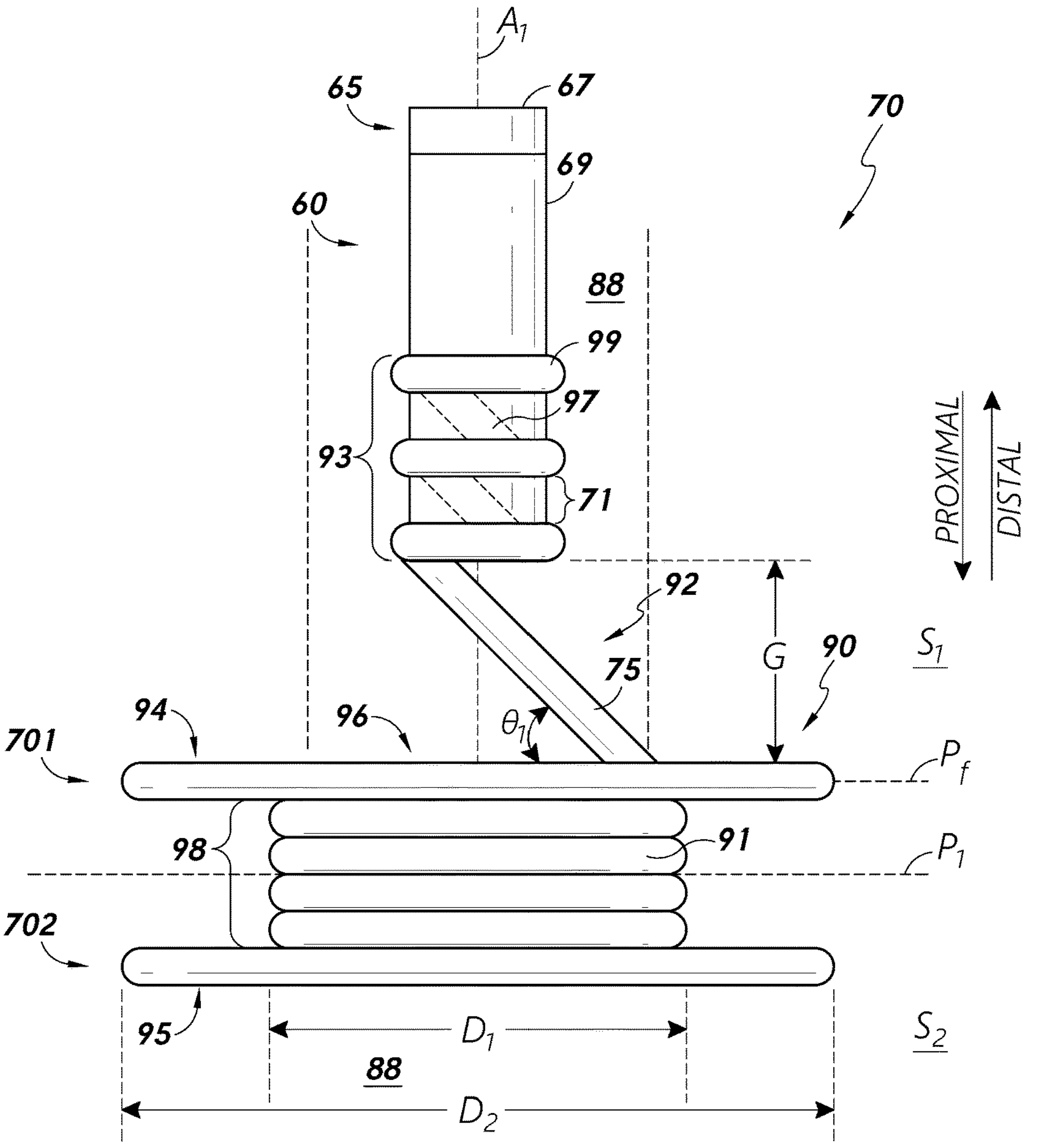
Figures 2, 7:
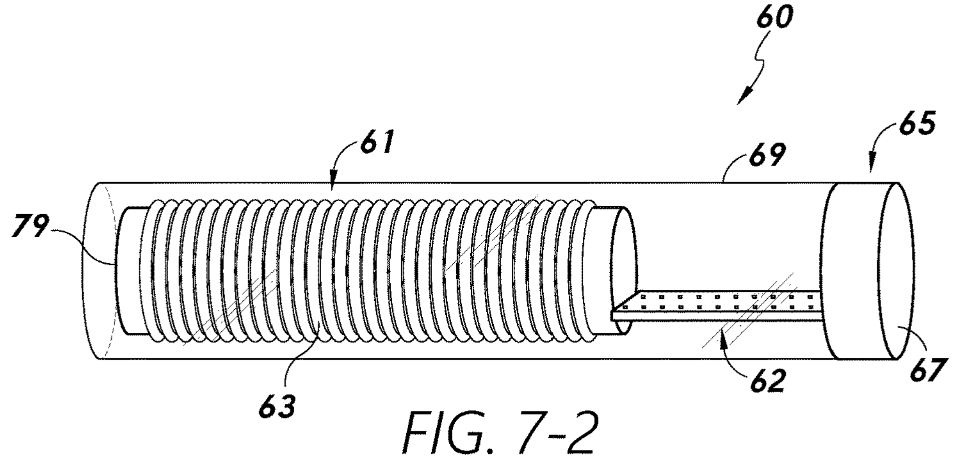
Figure 8A:
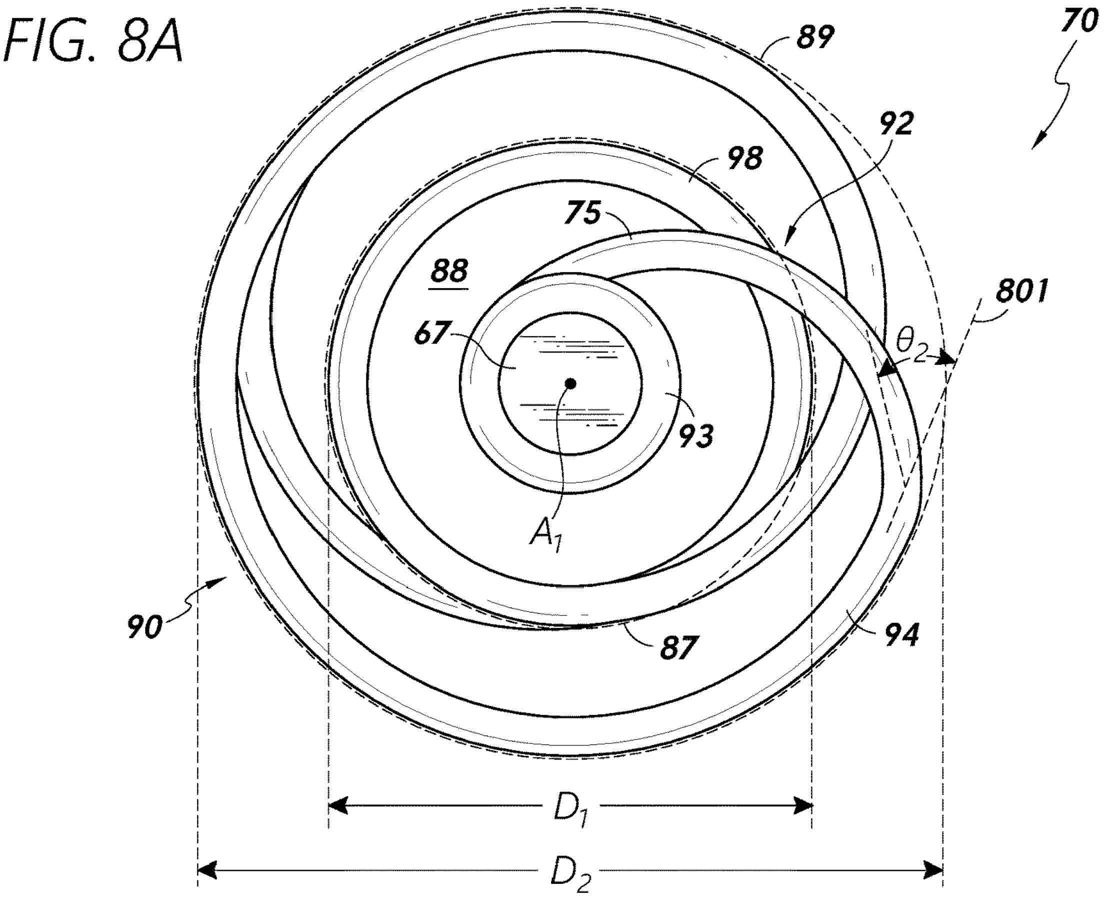
FIGS. 8A and 8B illustrate axial views an embodiment of a shunt-type sensor implant device in accordance with one or more embodiments.
Figure 8B:
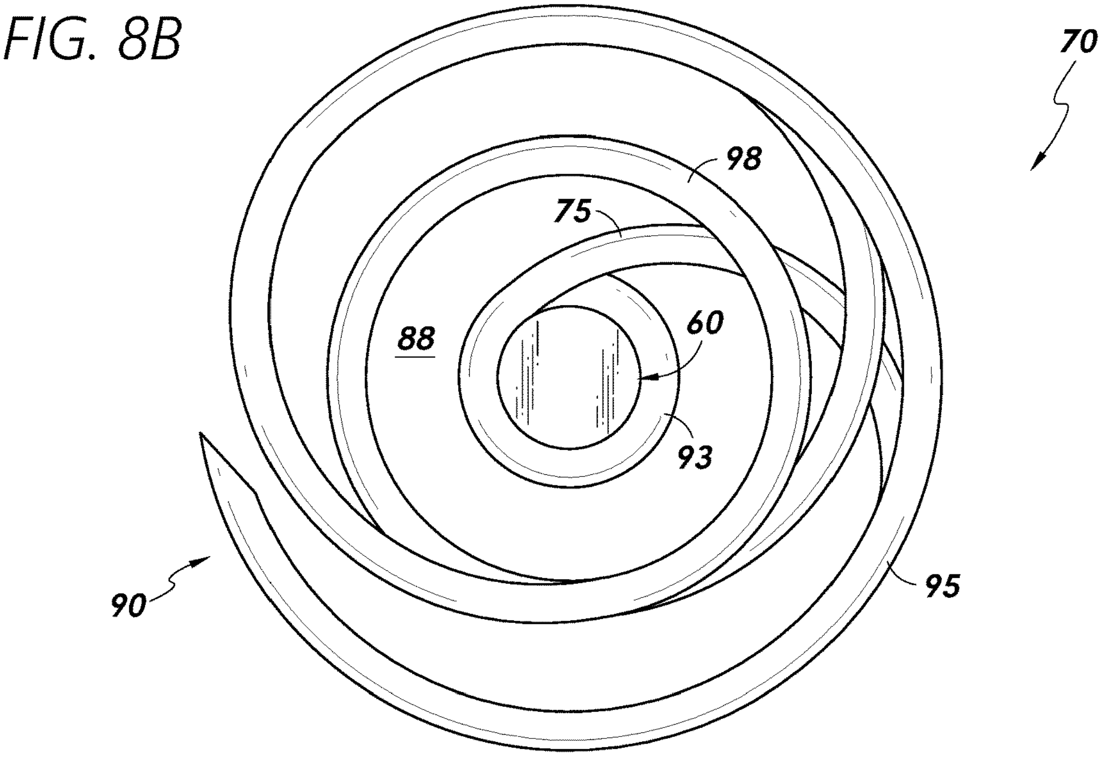

As referenced above, shunt and other implant devices/structures may be integrated with sensor, antenna/transceiver, and/or other components to facilitate in vivo monitoring of pressure and/or other physiological parameter(s). Sensor devices in accordance with embodiments of the present disclosure may be integrated with cardiac shunt structures/devices or other implant devices using any suitable or desirable attachment or integration mechanism or configuration. FIG. 7-1 illustrates a side view of a sensor implant device 70 in accordance with one or more embodiments. FIG. 7-2 illustrates an example sensor assembly/device 60 that can be a component of a sensor implant device, such as the sensor implant device 70 shown in FIG. 7-1. FIGS. 8A and 8B illustrate axial views of the shunt-type sensor implant device 70 of FIG. 7-1 in accordance with one or more embodiments.

The sensor implant device 70 comprises a shunt structure 90, which may have a coil form including one or more wires or other material or structure shaped into one or more winds of coil forming a fluid conduit/barrel portion 98 and axial end flanges 94, 95. Although described as flanges herein, it should be understood that such features may be any type of anchor structures configured to secure a shunt structure/body in a position in a tissue wall. The shunt structure 90 may represent an embodiment of a cardiac implant (e.g., anchor and/or cardiac implant structure 39 associated with FIG. 5 or 6) that may be integrated with pressure sensor functionality in accordance with certain embodiments disclosed herein. The shunt structure 90 is configured to hold a sensor device 60 configured to provide sensor readings relating to one or more physiological parameters associated with a target implantation site.

The sensor device 60 may be associated with either axial side/end of the shunt structure 90, wherein the different axial sides/ends of the shunt structure 90 are exposed on opposite sides ($S_1$, $S_2$) of a tissue wall when the implant device 70 is implanted in the tissue wall. As described herein, references to axial sides of a shunt structure may refer to opposite sides of a plane $P_1$ axially (and/or diagonally) bisecting the shunt structure 90 and/or barrel portion 98 thereof. The plane $P_1$ may be orthogonal to an axis of the barrel portion 98 of the shunt structure 90 and/or may be substantially parallel with (e.g., on/within) a tissue wall in which the shunt structure 90 is configured to be implanted. Description herein of axial sides of an implant structure can be understood to refer to different sides of the tissue-engagement plane $P_1$. The plane $P_1$ may be aligned (e.g., within 5° or 10° of exact alignment) with at least some of the coils/winds 91 of the barrel/conduit portion 98 of the shunt structure 90.

Furthermore, description herein of sensor devices and/or sensor arms being disposed on different radial sides of a shunt structure may refer to diametrically opposite sides of a diametrical plane $P_2$, as shown in FIG. 7-1. For example, where a shunt structure includes sensor arms on a given axial side of the shunt structure that emanate from substantially opposite circumferential portions of a barrel/conduit portion of the shunt structure and/or project in substantially opposite radial directions with respect to an axis of the barrel/conduit of the shunt structure, such arms may be considered to be on, or emanate from, different and/or opposite radial sides of the shunt structure.

The barrel portion 98 of the shunt structure 90 may advantageously be self-adjusting with respect to an axial length thereof. For example, the shape/form of the helical wire coil can allow for the barrel 98 to be axially expanded, thereby introducing gaps between adjacent winds 91 of the coil barrel 98. Therefore, the shunt structure 90 may be configured to be implanted in range of anatomies and or tissue walls having various characteristics and/or dimensions. In some embodiments, the barrel coil 98 is biased in an axially compacted configuration, as shown in FIG. 7-1, in which adjacent winds of the coil are in contact or relatively close proximity with each other. The barrel portion 98 may be considered a body portion of the shunt structure 90.

The sensor device 60 may advantageously be disposed, positioned, secured, oriented, and/or otherwise situated in a configuration in which the sensor transducer component 65 thereof is disposed within a channel area 88 of the shunt structure 90. The term "channel area" is used herein according to its broad and ordinary meaning and may refer to a three-dimensional space defined by a radial boundary of a fluid conduit and extending axially from the fluid conduit. For example, with respect to a given fluid conduit structure, such as the fluid conduit/barrel structure 98 of the shunt structure 90, a channel area 88 associated therewith may be considered to be defined according to any of the illustrated and described channel areas shown in FIGS. 9-1A, 9-1B. 9-2, 9-3A, and 9-3B.

The shunt structure 90 may be a radially expandable shunt. When expanded, a central flow channel 96 of the shunt 90 may define a generally circular or oval opening. The channel 96 may be configured to hold the sides of a puncture opening in a tissue wall to form a blood flow path between chamber(s) or vessel(s) of the heart (or other anatomy) that are separated by the tissue wall. For example, the shunt structure 90 may be configured to be implanted in the wall separating the coronary sinus and the left atrium. The central flow channel 96 may be partly formed by one or more winds 91 of the coliform structure 90. In some embodiments, substantially the entire shunt 90 is formed by super-elastic wire(s) (e.g., memory metal; nitinol) that is/are configured to be radially and/or otherwise compressed and fit into a catheter (not shown) and subsequently expanded back to the relaxed shape as shown in FIG. 7-1.

The shunt structure/frame 90 may have a helical shape in one or more portions thereof, including one or more distal and/or proximal curved arms at one or both ends of the frame 90, which may form the respective flanges 94, 95, at least in part. The shape of the barrel 98 and/or flange 94, 95 portions of the shunt structure/frame 90 may be pre-shaped to assume the deployed form of FIG. 7-1 when deployed from a delivery system/catheter. For example, the shunt structure wireform(s) can be constrained or compressed for insertion into the delivery system/catheter, wherein such compression is reversed substantially automatically when the shunt structure 90 is deployed from the catheter/system.

Formation of the shunt 90 using one or more elongate wires may serve to at least partially increase the flexibility of the shunt, thereby enabling compression thereof and expansion at the implant site. As mentioned above, the coil form shunt structure 90 may include a barrel/body portion 98 and one or more flange portions 94, 95. For example, in some embodiments, the barrel portion 98 may include one or more winds 91 of coil having a diameter $D_1$, wherein the wind(s) 91 define a barrel or fluid conduit structure 98 through which fluid may be shunted in accordance with aspects of the present disclosure. That is, the inside of the barrel 98 and/or coil winds 91 can define a fluid pathway/conduit. In some embodiments, such conduit 98 is substantially fluid tight. For example, the winds 91 may be compressed tightly enough together in the deployed configuration shown in FIG. 7-1 to substantially prevent leakage of fluid (e.g., blood) through the barrel portion 98. In some embodiments, some amount of fluid leakage between the coil winds 91 is permitted in the implanted/deployed configuration. The diameter $D_1$ of the shunt barrel 98 may have any suitable or desirable dimension, such as, for example, approximately 20 mm or less, such as approximately 10 mm or less (e.g., 7.5 mm). In some embodiments, gap(s) may be present between the winds 91 of the barrel portion 98 of the shunt structure 90 between at least one adjacent pair of winds 91, and/or between a wind 91 of the barrel portion 98 and one or more of the flange portions 94, 95 adjacent thereto.

The coil winds 91 forming the central flow channel 96 advantageously provide a tube having sufficient rigidity and structure to hold the tissue at the puncture site in an open position. The barrel portion 98 extends axially between the distal 94 and proximal 95 flanges, or coils, on each side. For example, the flange portions 94, 95 of the coil form 90 can generally be associated with proximal and distal axial ends, respectively, of the shunt structure 90. In some embodiments, the flange portions 94, 95 are configured to serve as tissue anchors to hold and/or pinch a tissue wall therebetween and/or otherwise prevent axial movement of the shunt structure 90 or dislodgment of the shunt structure 90 from the tissue wall in which it is implanted. For example, one or both of the flanges 94, 95 may have a coil form having a diameter $D_2$ that is greater than the diameter $D_1$ of the barrel 98, such that when the implant structure 90 is implanted sufficiently tightly within a tissue wall, with the barrel 98 occupying, at least in part, an area within/through the tissue wall, the expanded diameter $D_2$ of the flange(s) prevents the barrel 98 and shunt structure 90 from passing through the opening in the tissue wall in one or more directions. The diameter $D_2$ of the flange(s) may have any suitable or desirable dimension, such as, for example, approximately 40 mm or less, such as approximately 30 mm or less (e.g., 10-15 mm). Although both proximal 95 and distal 94 flange portions are shown in FIG. 7-1 and described in connection with various embodiments disclosed herein, it should be understood that sensor implant devices having anchor flanges in accordance with aspects of the present disclosure may include a flange on only one axial end of a shunt structure in some embodiments. Although distal and proximal sides/portions of shunt structures are described in some contexts herein, it should be understood that identified distal portions/sides may be outlet or inlet sides of the relevant shunt structure, as with identified proximal portions/sides. Furthermore, the terms "distal" and "proximal" are used for convenience and may or may not refer to relative orientation with respect to a delivery system/device used to implant the relevant sensor implant device and/or shunt structure.

Although certain embodiments of shunt structures disclosed herein comprise flow channels having substantially circular cross-sections, in some embodiments, shunt structures in accordance with the present disclosure have oval-shaped, rectangular, diamond-shaped, or elliptical flow channel configurations. For example, the one or more coils/winds 91 or other structural features of the shunt structure 90 of FIG. 7-1 can form an oval, circular, oblong, and/or elliptical cylindrical fluid conduit. It should be understood that references herein to fluid conduits, cylinders, and/or barrel structures of, and/or formed by, a shunt structure may have any axial cross-sectional shape.

In some embodiments, each of the distal and proximal flanges/coils 94, 95 is configured to radiate outward in a spiral form from the perimeter 87 of the barrel 98. Such spiral flange coils/wires 94, 95 can be shape-set to lie in a flange plane $P_1$ in the expanded/deployed configuration shown in FIG. 7-1. The expanded flanges/coils 94, 95 may serve to secure the shunt 90 to the target tissue wall. Although certain embodiments are disclosed herein in the context of shunt structures similar to that shown in FIG. 7-1, it should be understood that shunt structures or other implant devices integrated with pressure sensor functionality in accordance with embodiments of the present disclosure may have any type, form, structure, configuration, and/or may be used or configured to be used for any purpose, whether for shunting or other purpose or functionality.

The coil form shunt 90 further includes one or more sensor arms 92, which may emanate from one or more of the flanges 94, 95. For example, where the shunt structure 90 comprises one or more coiled wires, such coil forms may have one or more wire ends, which may generally be associated with either or both of the proximal 702 and distal 701 ends and/or associated flanges of the shunt structure 90. One or more of such wire end portions may be implemented as a sensor arm configured to hold and retain a sensor device 60 for the purpose of facilitating physiological parameter monitoring/sensing in accordance with aspects of the present disclosure. With respect to the illustrated embodiment of FIG. 7-1, the sensor arm 92 may include an extension/base portion 75, which may generally extend over the channel area 88 of the barrel 98 of the shunt structure 90 such as to allow for the positioning of the sensor device 60 held and/or retained by the sensor arm 92 generally within the channel area 88, at least in part.

In some embodiments, the sensor arm 92 is deflected axially with respect to the tissue-engagement plane $P_1$ of the shunt structure 90 and/or the plane $P_f$ of the flange 94 from which the arm 92 emanates by an amount/angle $\theta_1$. Although FIG. 7-1 shows the sensor implant device 70 in a configuration in which the sensor arm 92 is axially deflected distally with respect to the tissue-engagement plane $P_1$, it should be understood that embodiments of the present disclosure may be implemented without such axial deflection. For example, the sensor arm 92 may lie substantially in the plane $P_f$ of the flange 94, such that the sensor 60 is held in a position axially closer to the barrel 98 than in other embodiments in which deployed shunt structures have axially deflected sensor arms as shown in FIG. 7-1.

Deflection of the sensor 60 and sensor arm 92 distally from the flange 94 can be important to provide a flow path for fluid being shunted around the sensor 60 and/or through the fluid conduit 98 of the shunt structure 90. For example, the sensor 92 may be deflected in a manner as to provide an axial gap G between the sensor 60 and/or sensor-retention portion 93 of the shunt structure 90 and the flange 94 and/or fluid conduit opening 96. The axial flow gap G can provide an area for the blood or other fluid to flow around the sensor arm 92 and into the opening 96 of the fluid conduit 98. The angle $\theta_1$ may be any desirable angle between the extension portion 75 of the sensor arm 92 and the tissue-engagement plane $P_1$ and/or plane $P_f$ of the flange 94. In some embodiments, the deflection angle $\theta_1$ is between about 30° and 60°, such as about 35°, 40°, or 45°. For embodiments in which the arm 92 is deflected by an angle greater than 90°, such implementations may place at least a portion of the sensor device 60 outside of the channel area 88. Therefore, it may be desirable to implement a sensor arm deflection angle $\theta_1$ that is less than 90° to maintain the sensor device 60 and/or transducer component 65 thereof within the channel area 88 of the shunt structure 90. Furthermore, by deflecting the sensor arm 92 in a manner as to position the sensor 60 at or near the center of the flow channel 88 and/or the axis $A_1$ of the fluid conduit 98, the fluid flow gap area may be maximized with respect to a given gap distance G. For example, in such embodiments, a substantially equal amount of blood flow may be permitted from around the perimeter 87 of the fluid conduit 98. In some embodiments, the arm 92 may be deflected in a manner as to position the sensor 60 and sensor arm 92 on one side or area of the fluid conduit 98 to allow for a greater area or amount of fluid flow in a desired area of the fluid conduit and/or from a desired direction.

FIG. 8A shows an axial view that corresponds to an axial side of the implant device 70 associated with the sensor device 60. That is, the sensor component 65 is attached to, integrated with, or otherwise associated with the arm 92, the side of which is shown facing out of the page in FIG. 8A. The side shown facing out of the page in FIG. 8A may be a distal or proximal side. FIG. 8B shows an axial view that corresponds to an axial side of the implant device 70 that is opposite the sensor device 60. The side shown facing out of the page in FIG. 8B may be a distal or proximal side.

As shown in FIG. 8A, the sensor arm 92 may further be radially deflected inward by an amount $\theta_2$ relative to a tangent line 801 of the flange coil 94 at the base of the extension portion 75 of the arm 92, wherein such radial deflection may serve to position the sensor 60 within the channel area 88, at least in part. For example, were the sensor arm 92 not deflected radially inward as in FIG. 8A, the sensor arm 92 would hold the sensor 60 in an area at or near the outer perimeter 89 of the flange 94, and possibly radially outside of the channel area 88, at least in part. By radially deflecting the arm 92, as shown in FIGS. 8A and 8B, the sensor arm 92 may project from the outer perimeter 89 of the flange 94 to an area within the channel area 88 of the barrel 98. In some embodiments, the sensor arm 92 is deflected radially by an amount sufficient to place the sensor 60 in substantial coaxial alignment with the axis $A_1$ of the barrel 98, although such coaxial alignment with the barrel 98 is not necessary and embodiments of the present disclosure may be configured such that the sensor device 60 is held in a position within the channel area 88 but at least partially off-axis with respect to the barrel 98.

The sensor arm 92 may further include a sensor-retention portion 93, which may comprise one or more wraps/winds 99 of the coil arm 92 in a relatively tightly-wrapped configuration around the body/housing 69 of the sensor device 60 to thereby restrain/retain, at least in part, the sensor device 60 and hold the sensor device 60 in the desired sensing position. It may be desirable for the winds 99 of the coil in the retention portion 93 of the sensor arm 92 to be sufficiently tight and/or secured to reduce the risk of dislodgment/escape of the sensor device 60 in the presence of fluid flow and/or other fluid conditions (e.g., pressure) in the implantation environment. Although FIG. 7-1 shows the sensor-retention portion 93 of the sensor arm 92 as comprising winds 99 of the coil form wrapped around the body 69 of the sensor 60, it should be understood that the sensor device 60 may be coupled to the sensor arm 92 in any suitable or desirable manner. The sensor device 60 may be secured to the anchor arm 94 using any suitable means or mechanism. For example, securement/attachment means/mechanisms that may be suitable for attaching the sensor device 60 to a sensor arm of the shunt structure 90 may be any of the features disclosed in PCT Application No. PCT/US20/56746, Filed on Oct. 22, 2020, and entitled "Sensor Integration in Cardiac Implant Devices," the contents of which are hereby expressly incorporated by reference in their entirety. For example, the shunt structure 90 and/or sensor arm(s) thereof may include one or more sensor-retention fingers, clamps, wraps, bands, belts, clips, pouches, housings, encasements, and/or the like configured to secure the sensor device 60 to an arm and/or strut or another structural feature of the shunt structure 90. For example, one or more clips, hooks, adhesives, or other attachment feature(s) may be associated with the sensor-retention portion 93 of the sensor arm 92, wherein such feature(s) are configured to secure the sensor 60 to the sensor arm 92.

In some embodiments, the sensor-retention portion 93 of the sensor arm 92 includes a plurality of coil winds 99 separated by gap(s) 71. Bridge wire portions 97 may connect between the coils 99, spanning the gap(s) 71. In some embodiments, no such gap(s) is/are present between adjacent sensor-retention coil winds 99.

With reference to FIG. 7-2, which shows a detailed view of an example embodiment of a sensor device 60 that may be associated with any of the sensor implant devices disclosed herein, such as the sensor implant device 70 shown in FIGS. 7-1, 8A, and 8B, in some embodiments, the sensor device/assembly 60 includes a sensor transducer component 65 and an antenna component 61. The sensor transducer component 65 may comprise any type of sensor transducer as described in detail above. In some embodiments, the sensor device 60 may be attached to or integrated with an arm member 92 of the shunt structure 90, as shown in FIGS. 7-1, 8A, and 8B.

The sensor transducer component 65 includes a sensor element 67, such as a pressure sensor transducer/membrane. As described herein, the sensor device 60 may be configured to implement wireless data and/or power transmission. The sensor device 60 may include the antenna component 61 for such purpose. The antenna 61, as well as one or more other components of the sensor device 60, may be contained at least partially within a sensor housing 69, which may further have disposed therein certain control circuitry 62 configured to facilitate wireless data and/or power communication functionality. In some embodiments, the antenna component 61 comprises one or more conductive coils/winds 67, which may facilitate inductive powering and/or data transmission. In embodiments comprising conductive coil(s), such coil(s) may be wrapped/disposed at least partially around a magnetic (e.g., ferrite, iron) core 79.

The sensor device 60 may advantageously be biocompatible. For example, the housing 69 may advantageously be biocompatible, such as a housing comprising glass or other biocompatible material. However, at least a portion of the sensor transducer element/membrane 67, such as a diaphragm or other component, may be exposed to the external environment in some embodiments in order to allow for pressure readings, or other parameter sensing, to be implemented. The housing 69 may comprise an at least partially rigid cylindrical or tube-like form, such as a glass cylinder form. In some embodiments, the sensor transducer component 65/67 is approximately 3 mm or less in diameter. The antenna 61 may be approximately 20 mm or less in length.

The sensor device 60 may be configured to communicate with an external system when implanted in a heart or other area of a patient's body. For example, the antenna 61 may receive power wirelessly from the external system and/or communicate sensed data or waveforms to and/or from the external system. The sensor element 67 may comprise a pressure transducer. For example, the pressure transducer may be a microelectromechanical system (MEMS) transducer comprising a semiconductor diaphragm component. In some embodiments, the transducer may include an at least partially flexible or compressible diaphragm component, which may be made from silicone or other flexible material. The diaphragm component may be configured to be flexed or compressed in response to changes in environmental pressure. The control circuitry 62 may be configured to process signals generated in response to said flexing/compression to provide pressure readings. In some embodiments, the diaphragm component is associated with a biocompatible layer on the outside surface thereof, such as silicon nitride (e.g., doped silicon nitride) or the like. The diaphragm component and/or other components of the pressure transducer 67 may advantageously be fused or otherwise sealed to/with the housing 69 of the sensor device 60 in order to provide hermetic sealing of at least some of the sensor components.

The control circuitry 62 may comprise one or more electronic application-specific integrated circuit (ASIC) chips or die, which may be programmed and/or customized or configured to perform monitoring functionality as described herein and/or facilitate transmission of sensor signals wirelessly. The antenna 61 may comprise a ferrite core 79 wrapped with conductive material in the form of a plurality of coils/winds 63 (e.g., wire coil). In some embodiments, the coils/winds comprise copper or other metal. The antenna 61 may advantageously be configured with coil geometry that does not result in substantial displacement or heating in the presence of magnetic resonance imaging. In some implementations, the sensor implant device 70 may be delivered to a target implant site using a delivery catheter (not shown), wherein the delivery catheter includes a cavity or channel configured to accommodate the advancement of the sensor device 60 therethrough.

Figures 3A, 9:
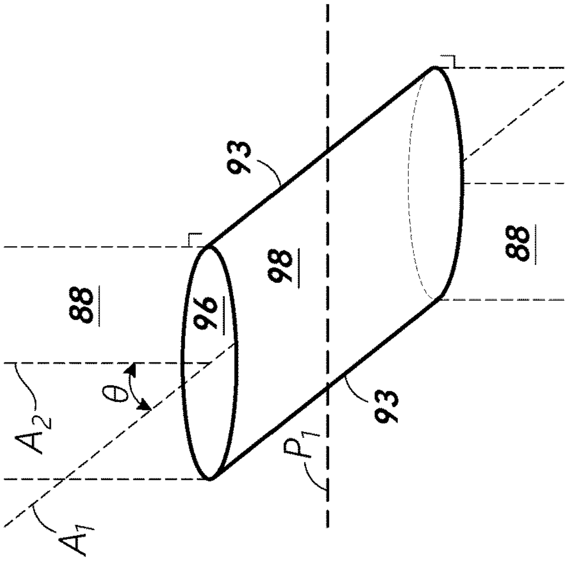
FIGS. 9-1A, 9-1B. 9-2, 9-3A, and 9-3B show example channel areas associated with respective shunt body fluid conduits in accordance with one or more embodiments.

As described above, some embodiments of the present disclosure include shunt structures having sensor arms configured to hold a sensor in a channel area of the shunt structure, which can advantageously facilitate sensing of fluid dynamics relating to fluid flow through the shunt structure. FIGS. 9-1A. 9-1B. 9-2, 9-3A, and 9-3B show example channel areas 88 associated with respective shunt body fluid conduits 98 in accordance with one or more embodiments. In particular, FIGS. 9-1A, 9-2, and 9-3A show side views of fluid conduits and associated channel areas, whereas FIGS. 9-1B, and 9-3B show axial and/or top-down views of the respective fluid conduits and channel areas.

Figures 3B, 9:
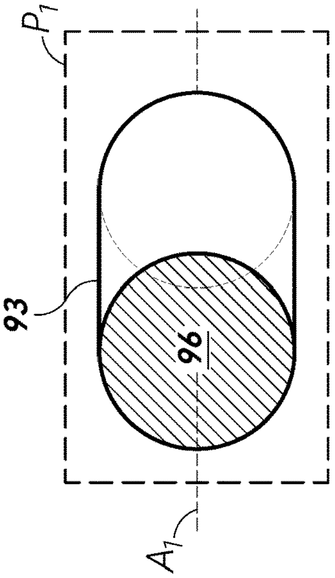
Figures 2, 9:
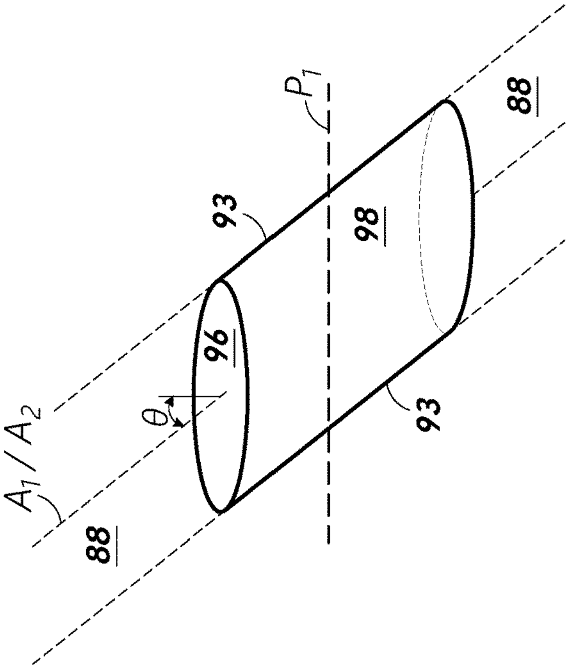
Figures 1A, 9:
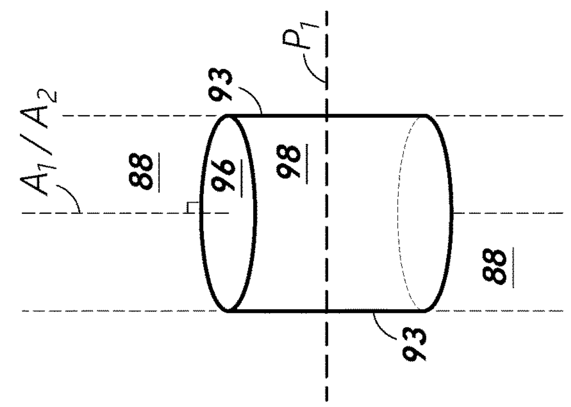
Figures 1B, 9:
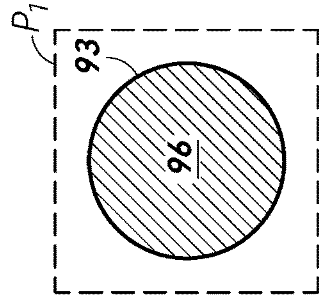

FIGS. 9-1A and 9-1B show an example fluid conduit 98 formed by one or more outer walls 93, wherein the fluid conduit 98 is associated with a tissue plane $P_1$. For example, as described above, the tissue plane $P_1$ may generally represent a plane that lies in or parallel to a tissue wall in which the fluid conduit 98 is configured to be implanted/disposed. For example, the fluid conduit 98 may represent a conduit structure (e.g., formed of a plurality of winds of a coil wireform) of a shunt implant device as described herein. In the particular embodiment of FIGS. 9-1A and 9-1B, the fluid conduit 98 has an axis $A_1$ that is generally orthogonal, perpendicular, and/or normal to the tissue plane $P_1$. In such an embodiment/configuration, the channel area 88 associated with the fluid conduit 98 can be considered to be a three-dimensional projection/extension of the area of the fluid conduit around the axis $A_1$, and bounded by the wall(s) 93, in one or more directions, as shown. Therefore, the channel area 88 may be a three-dimensional area enclosed by a cylinder having the same axial cross-sectional area as the fluid conduit 98 and being disposed about the axis $A_1$ of the fluid conduit 98. A sensor transducer disposed within the channel area 88 of the fluid conduit 98 shown in FIGS. 9-1A and 9-1B may be considered to be disposed in an area defined by the radial boundary of the fluid conduit 98 around the axis $A_1$ of the fluid conduit 98. Furthermore, the sensor transducer may be disposed in an area of the channel area 88 that is axially outside of the fluid conduit structure 98, as with the illustrated sensor implant device 70 shown in FIG. 7-1, wherein the sensor transducer 65 is disposed in the channel area 88 axially outside of the shunt barrel structure 98.

FIG. 9-2 shows another example fluid conduit 98 formed by one or more outer walls 93, wherein the fluid conduit 98 is associated with a tissue plane $P_1$, which may be defined/represented in a manner as described in detail above. The fluid conduit 98 of the embodiment of FIG. 9-2 may be configured to be implanted in a tissue wall (e.g., tissue wall coplanar with the tissue plane $P_1$), wherein an axis $A_1$ of the fluid conduit 98 is angled with respect to the tissue plane $P_1$ (i.e., the axis $A_1$ of the conduit 98 is not perpendicular, orthogonal, or normal to the tissue plane $P_1$). That is, the fluid conduit 98 may be an oblique cylinder, as shown. Therefore, in some embodiments, with respect to an oblique/angled fluid conduit 98 as shown in FIG. 9-2, a channel area 88 associated therewith may be considered a three-dimensional area defined by the radial boundary of the fluid conduit 98 about the axis $A_1$ of the fluid conduit extending in one or more directions axially away from the fluid conduit 98, such that the boundary of the channel area 88 is defined by a cylinder that has an axis that is angled with respect to the tissue plane $P_1$, as shown.

FIGS. 9-3A and 9-3B show another example fluid conduit 98 formed by one or more outer walls 93, wherein the fluid conduit 98 is associated with a tissue plane $P_1$, which may be defined/represented in a manner as described in detail above. The fluid conduit 98 of the embodiment of FIGS. 9-3A and 9-3B may be configured to be implanted in a tissue wall (e.g., tissue wall coplanar with the tissue plane $P_1$) wherein an axis $A_1$ of the conduit 98 is angled with respect to the tissue plane $P_1$ (i.e., the axis $A_1$ of the conduit 98 is not perpendicular, orthogonal, or normal to the tissue plane $P_1$). However, it may be desirable to identify the channel area 88 associated with the fluid conduit 98 as being a channel area having an axis $A_2$ (with respect to FIGS. 9-1A. 9-1B, 9-2, 9-3A, and 9-3B, $A_1$ represents the axis of the respective fluid conduit, whereas $A_2$ represents the axis (or axes) of the channel area 88 of the fluid conduit; in some cases $A_1$ and $A_2$ may be the same) that is parallel, orthogonal, and/or normal to the plane $P_1$, as shown. Therefore, the channel area 88 of FIGS. 9-3A and 9-3B may not be coaxial with the conduit 98, but rather may be defined on one end by the radial boundary of the opening 96 of the conduit 98, wherein the channel area 88 extends therefrom in an orientation/direction that is perpendicular, orthogonal, and/or normal to the plane $P_1$, as shown in FIGS. 9-3A and 9-3B. The channel area 88 identified in FIGS. 9-3A and 9-3B may correspond to a primary orientation/path of a true flow channel of fluid that may flow through the fluid conduit 98 when the conduit 98 is implanted in a tissue wall between two blood vessels/chambers. That is, fluid may flow into the opening 96 of the fluid conduit 98 primarily in a direction that is perpendicular to the tissue plane $P_1$ in some cases.

Figure 10:
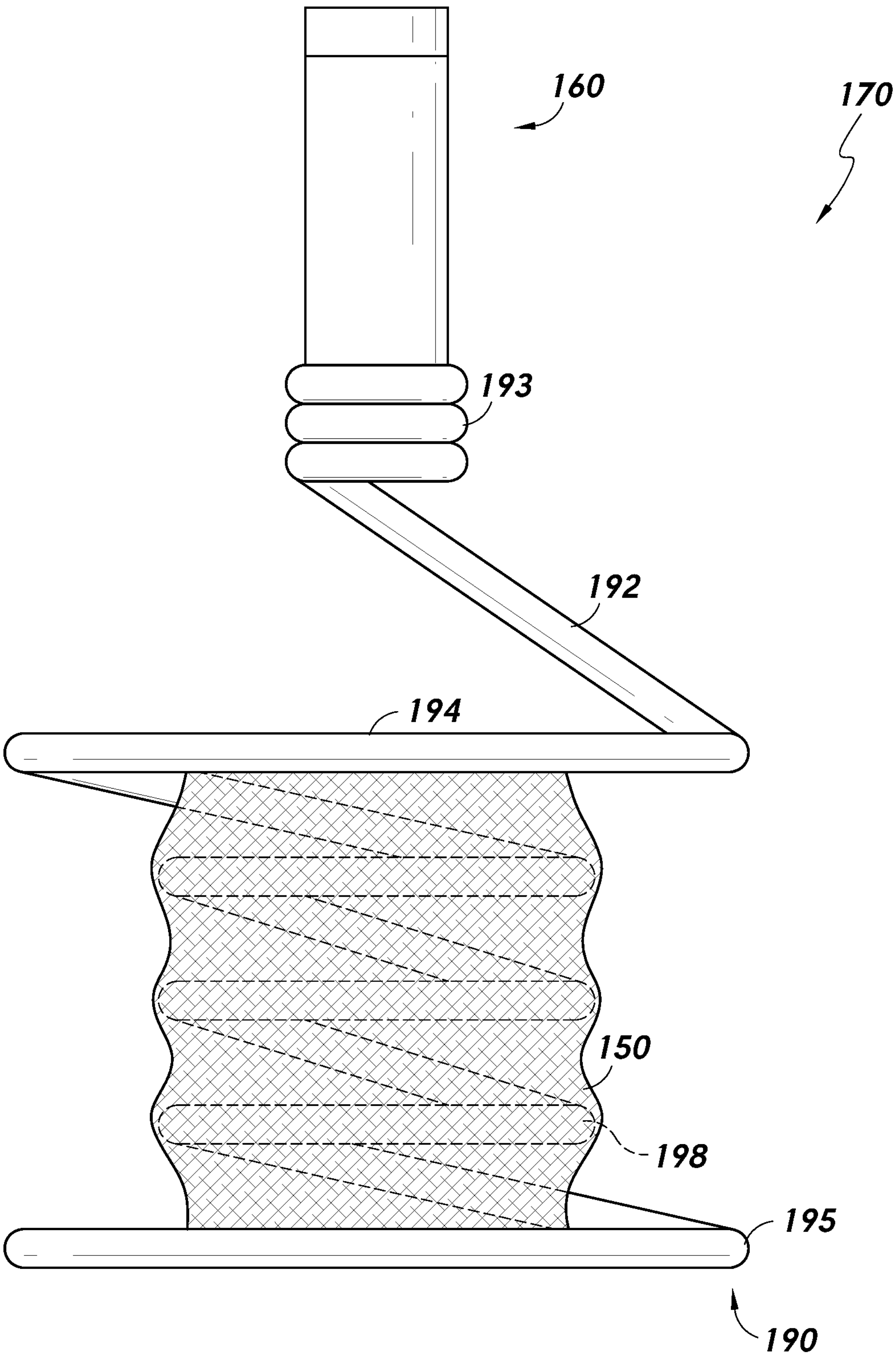
FIG. 10 shows a sensor implant device having a barrel cover associated therewith in accordance with one or more embodiments.

FIG. 10 shows a sensor implant device 170 having a barrel cover 150 associated therewith in accordance with one or more embodiments. The sensor implant device 170 may be similar in certain respects to any of the embodiments of sensor implant devices disclosed herein. For example, the sensor implant device 170 may include a barrel portion 198 and one or more flange portions 194, 195, wherein such portions of the implant device 170 are formed of respective winds of coil of a coil/wireform shunt structure 190.

As referenced, the sensor implant device 170 includes a seal or cover 150, which may comprise any suitable or desirable material and/or structure/form, such as, cloth/fabric, polymer, mesh, or the like formed of any type of material. The cover 150 can be disposed over one or more portions or areas of the shunt structure 190. For example, as shown in FIG. 10, the cover 150 may be disposed over and/or within the barrel portion 198 of the shunt structure 190. Although the cover 150 is illustrated as being disposed around an outside of the barrel 198, it should be understood that embodiments of the present disclosure may include covers disposed inside the barrel portion of a shunt structure.

In some embodiments, the cover 150 is at least partially fluid-tight, such that the cover 150 serves to prevent or reduce fluid leakage outside of the implant device 170 when implanted. Furthermore, in some embodiments, the cover 150 may be configured to facilitate or promote tissue ingrowth between the implant device 170 and the surrounding tissue of the tissue wall in which the implant device 170 is implanted. Although illustrated as a covering/skirt-type structure, the cover 150 may be a coating or other application to the wireform shunt structure 190 (e.g., to the barrel 198) in some implementations. The cover 150 is advantageously biocompatible to allow for prolonged maintenance of the implant device 170 in the implanted location.

FIGS. 11A and 11B show side and axial views, respectively, of a sensor implant device 50 having a dual-arm sensor holder in accordance with one or more embodiments. The sensor implant device 50 may be similar in certain respects the sensor implant device 70 shown in FIG. 7-1 and described in detail above. For example, the sensor implant device 50 of FIGS. 11A and 11B can comprise one or more wireforms formed into a barrel portion 28, and distal 24 and/or proximal 25 flange portions. Furthermore, the implant device 50 may include a sensor arm 22 including a base or extension portion 76 and a sensor-retention portion 23. The arm 22 may emanate from the distal flange 24 and/or a spiraling wire **24*a* associated therewith in the manner as described above with respect to FIG. 7-1**.

The sensor implant device 50 can further include a second sensor arm 27, which may be configured to secure and/or hold, at least in part, the sensor device 60, such as in the area of the sensor-retention portion 23 of the sensor arms 22, 27. In some embodiments, the second sensor arm 27 may be similar to the first sensor arm 22, and may emanate from an opposite side and/or circumferential area of the flange 24 and/or shunt structure 20, which may advantageously provide a desirable degree of stability for sensor retention. For example, in single-arm embodiments as shown in FIG. 7-1, such sensor arm may be prone to post-implantation arm deflection caused by certain fluid dynamics (e.g., flow, pressure, etc.) at the implantation site, which may affect sensor readings and/or compromise the structural integrity of the shunt structure. Therefore, embodiments having more than one sensor arm, such as the embodiment shown in FIGS. 11A and 11B, can provide increased stability. Such embodiments may prevent and/or reduce post-implantation movement or deflection of the sensor 60 and/or associated support arm(s).

In some embodiments, the second sensor arm 27 may have a radial deflection $\theta_3$ that is similar to the deflection $\theta_2$ of the first sensor arm 22. Although two arms 22, 27 are shown in FIGS. 11A and 11B, it should be understood that embodiments of the present disclosure may have any suitable or desirable number of sensor arms, including three arms, four arms, or more.

In some embodiments, the shunt structure 20 and/or the sensor arms 22, 27 arc formed from multiple/separate wires, rather than a single common wire as with certain other embodiments. For example, the shunt structure 20 may be made up of at least two separate wires, which may be coiled/wound together to provide the shunt structure 20. In some such embodiments, both/all wires may traverse the barrel portion 28 and may each have an end on each axial side of the shunt structure 20. In some embodiments, two separate wires of the shunt structure 20 may be helical in the same direction (e.g., both clockwise or counterclockwise winding in a given axial direction), or may be wound/coiled in opposite directions.

In some embodiments, the two sensor arms 22, 27 are associated with opposite ends of the same wire. For example, such wire may be wrapped around the sensor 60 in the sensor-retention portion 23 at the sensor arm 22, and traverse the distal flange 24, barrel 28, proximal flange 25, and back, terminating at the end of the sensor arm 27 in the sensor-retention area/portion 23. In some embodiments, the ends of the wire are not in the area of the sensor arms 22, 27 (e.g., not in the sensor-retention area/portion 23), but rather in another area of the shunt structure 20, such as at or near the proximal flange 25. For example, the wire may start at the proximal end/flange 25 and traverse to the sensor-retention portion 23 through the barrel 98, flange 24, and sensor arm 22, wherein the wire is wrapped around the sensor 60 in the sensor-retention area 23 and travels/traverses back to the proximal end 25 via the sensor arm 27, flange 24, and barrel 28 in the proximal direction. It should be understood that the shunt structure 20 can comprise any number of wires, and such wire(s) can be wound to form the proximal flange 25 barrel 28, distal flange 24, and the sensor arms 22, 27, including the sensor-retention form/structure 23, in any suitable or desirable way.

Figure 12A:
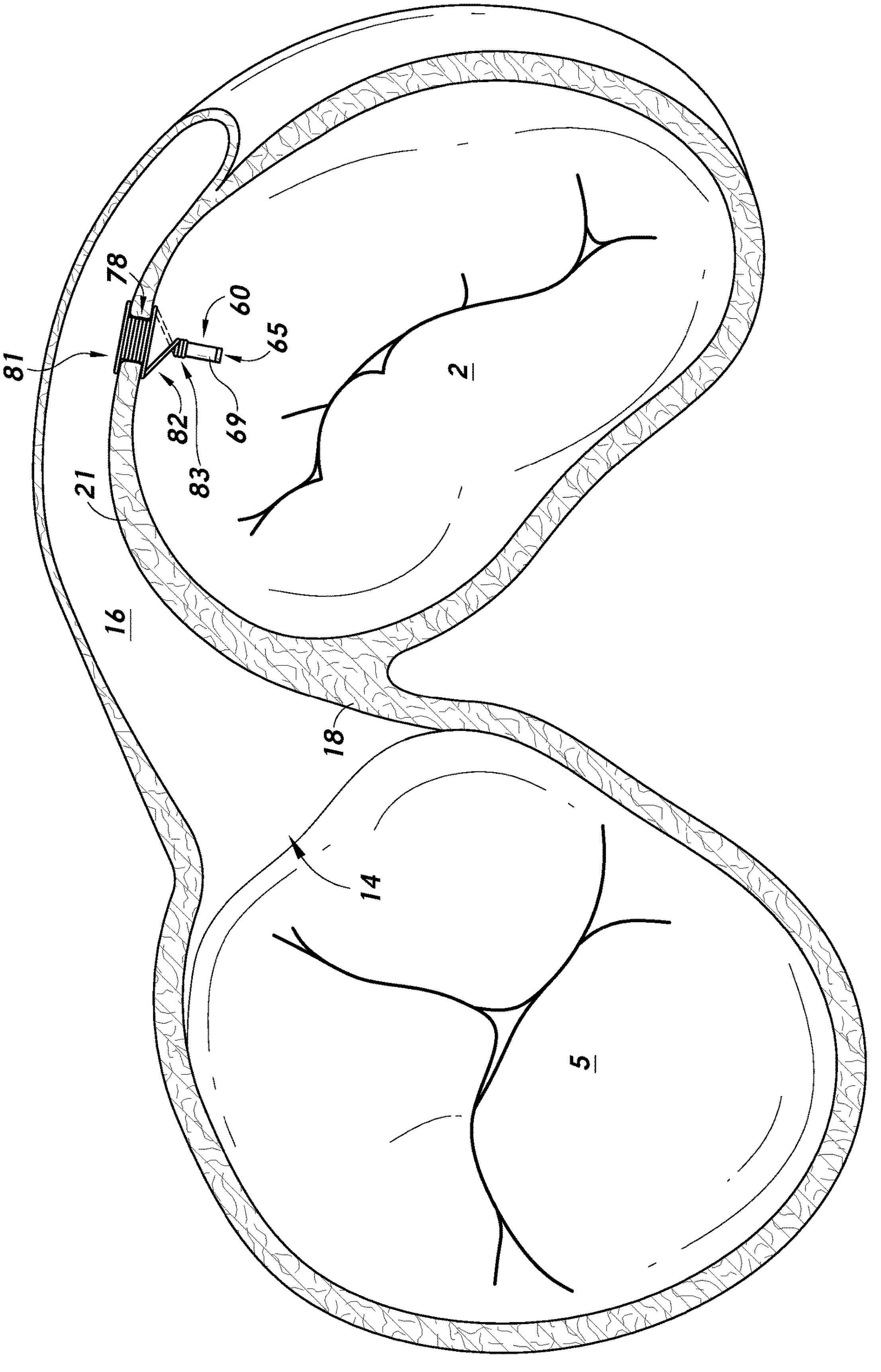
FIGS. 12A and 12B show a sensor implant device implanted in a coronary sinus tissue wall in accordance with one or more embodiments.
Figure 12B:
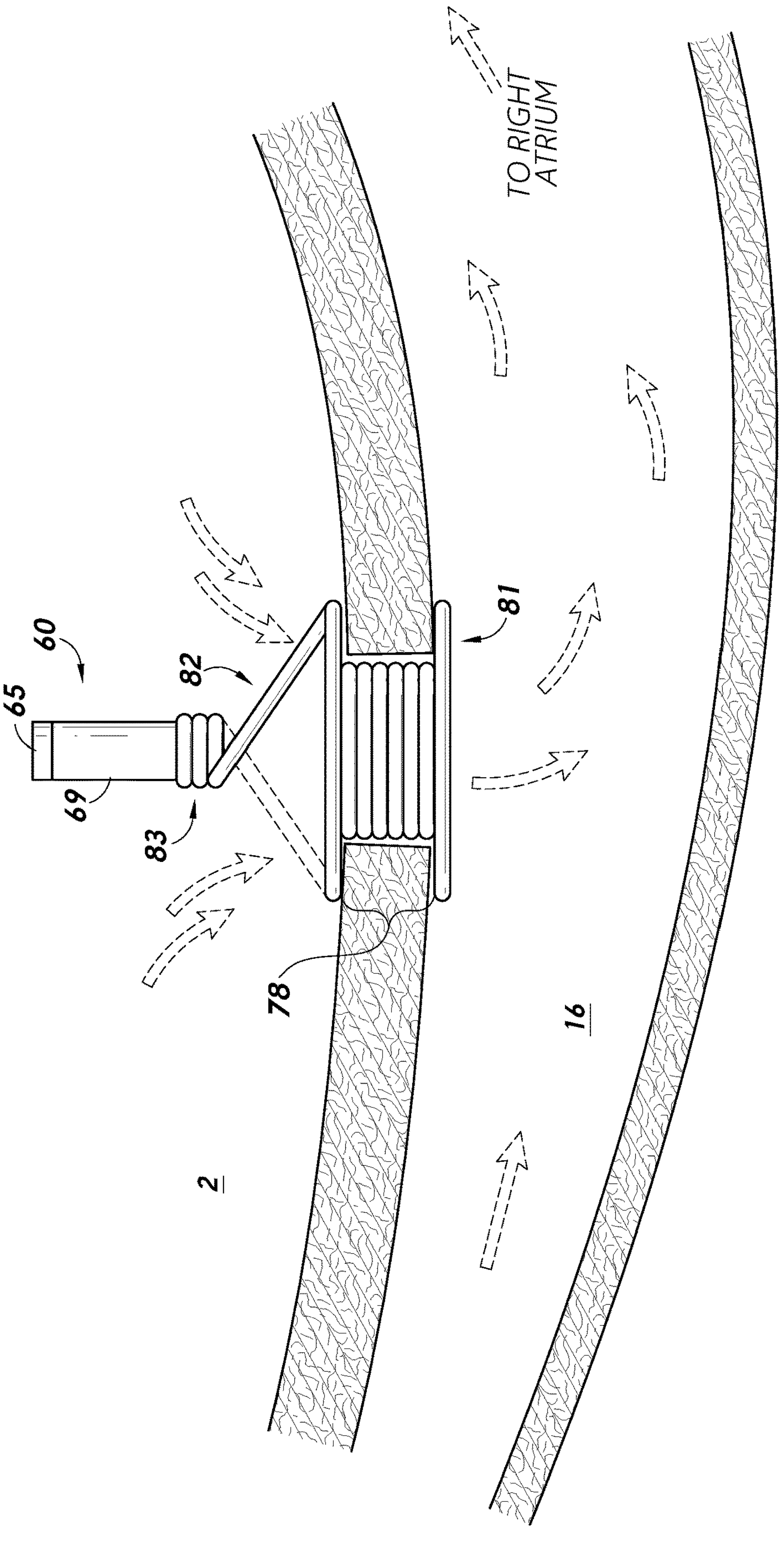

In some implementations, shunt devices/structures in accordance with embodiments of the present disclosure may be implanted in a wall separating the coronary sinus from the left atrium, such that interatrial shunting may be achieved through the coronary sinus. FIGS. 12A and 12B show a shunt-type sensor implant device 80 implanted in a tissue wall 21 between the coronary sinus 16 and the left atrium 2. FIG. 12, as well as a number of the following figures, shows a section of the heart from a top-down, superior perspective with the posterior aspect oriented at the top of the page.

In some cases, left-to-right shunting through implantation of the shunt device 80 in the wall 21 between the left atrium 2 and the coronary sinus 16 can be preferable to shunting through the atrial septum 18. For example, shunting through the coronary sinus 16 can provide reduced risk of thrombus and embolism. Generally, the coronary sinus can be less likely to have thrombus/emboli present for several reasons. First, the blood draining from the coronary vasculature into the right atrium 5 has just passed through capillaries, so it is essentially filtered blood. Second, the ostium 14 of the coronary sinus in the right atrium is often partially covered by a pseudo-valve called the Thebesian valve (not shown). The Thebesian valve is not always present, but some studies show it is present in most hearts and can block thrombus or other emboli from entering in the event of a spike in right atrial pressure. Third, the pressure gradient between the coronary sinus and the right atrium into which it drains is generally relatively low, such that thrombus or other emboli in the right atrium is likely to remain there. Fourth, in the event that thrombus/emboli do enter the coronary sinus, there is typically a much greater gradient between the right atrium and the coronary vasculature than between the right atrium and the left atrium. Most likely, thrombus/emboli would travel further down the coronary vasculature until right atrium pressure returned to normal and then the emboli would return directly to the right atrium.

Some additional advantages to locating the sensor implant device 80 in the wall between the left atrium and the coronary sinus relate to the consideration that such anatomy is generally more stable than the interatrial septal tissue. By diverting left atrial blood into the coronary sinus, sinus pressures may increase by a small amount. This can cause blood in the coronary vasculature to travel more slowly through the heart, possibly increasing perfusion and oxygen transfer, which can be more efficient and also can help a dying heart muscle to recover. In addition, by implanting the shunt device/structure 83 in the wall of the coronary sinus, damage to the atrial septum 18 may be prevented. Therefore, the atrial septum 18 may be preserved for later transseptal access for other therapies. The preservation of transseptal access may be advantageous for various reasons. For example, heart failure patients often have a number of other comorbidities, such as atrial fibrillation and/or mitral regurgitation; certain therapies for treating these conditions require a transseptal access.

It should be noted, that in addition to the various benefits of placing the sensor implant device 80 between the coronary sinus 16 and the left atrium 2, certain drawbacks may be considered. For example, by shunting blood from the left atrium 2 to the coronary sinus 16, oxygenated blood from the left atrium 2 may be passed to the right atrium 5 and/or non-oxygenated blood from the right atrium 5 may be passed to the left atrium 2, both of which may be undesirable with respect to proper functioning of the heart.

With further reference to FIGS. 12A and 12B, the coronary sinus 16 is generally contiguous around the left atrium 2, and therefore there are a variety of possible acceptable placements for the implant device 80. The target site selected for placement of the implant device 80 may be made in an area where the tissue of the particular patient is less thick or less dense, as determined beforehand by non-invasive diagnostic means, such as a CT scan or radiographic technique, such as fluoroscopy or intravascular coronary echo (IVUS).

As with other embodiments, the sensor implant device 80 includes a sensor device 60 having a sensor transducer component 65 and certain connectivity component(s) (e.g., an antenna component and/or other control circuitry). The sensor implant device 80 is disposed, attached, and/or otherwise secured to or associated with one or more sensor arms 82 of an implant structure 81 (e.g., shunt structure) of the sensor implant device 80 in a manner such that the sensor transducer 65 is disposed within or near a channel area associated with the barrel/conduit portion 78 of the shunt structure 81. For example, the implant device 80 may be configured such that the sensor transducer component 65 is at least partially exposed on the atrial side of the tissue wall 21, as shown. With the sensor transducer component 65 disposed in the channel area of the shunt conduit 78, the sensor transducer 65 may advantageously be disposed in an area of flow that is relatively high, thereby allowing for sensor readings to be generated indicating characteristics of the flow through the conduit 78 of the shunt structure 81.

Figure 13:
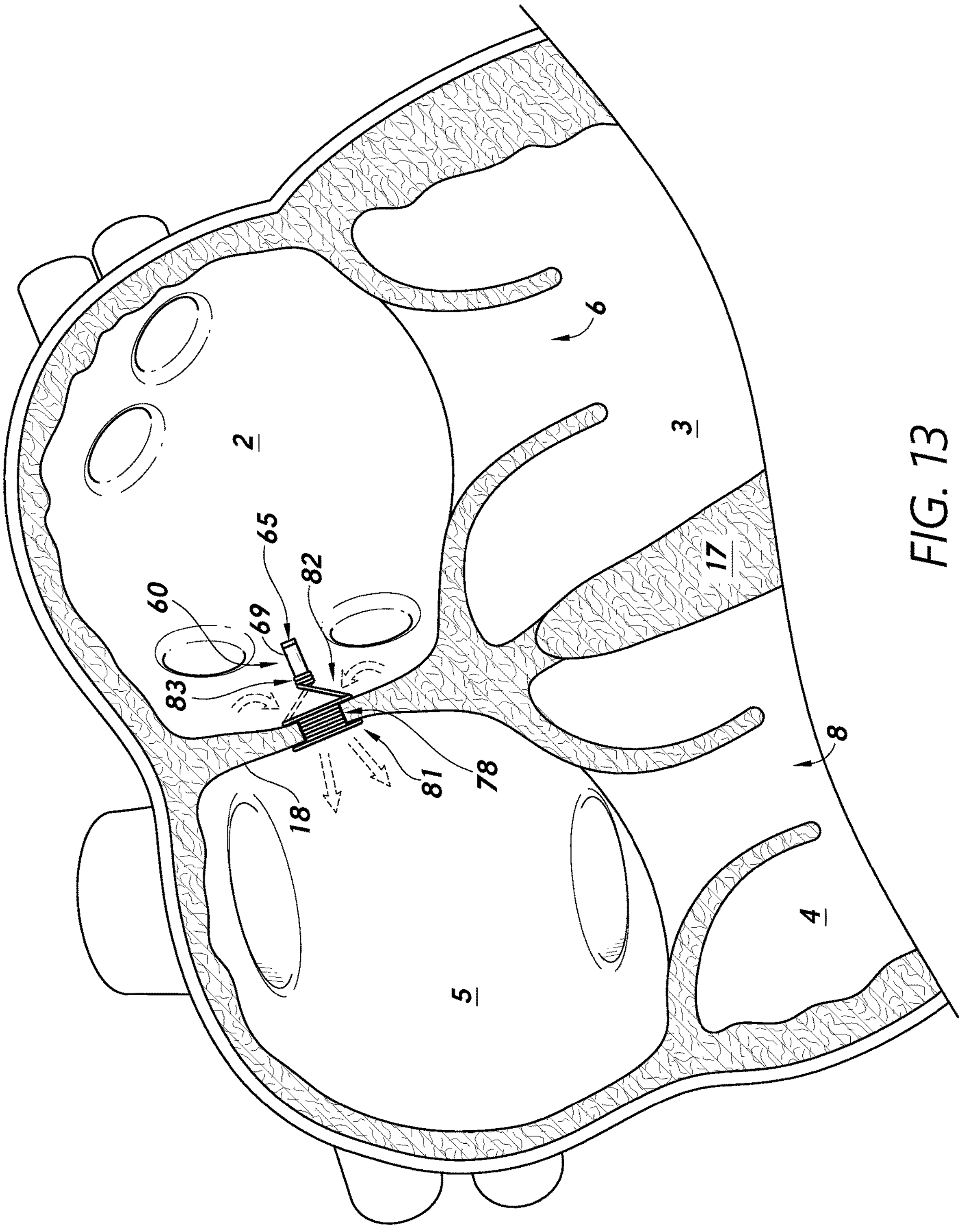
FIG. 13 shows a sensor implant device implanted in an atrial septum with a sensor of the device exposed in a left atrium in accordance with one or more embodiments.

FIG. 13 shows a sensor implant device 80 implanted in an atrial septum 18 in accordance with one or more embodiments. The particular position in the atrial septum wall 18 may be selected or determined to provide a relatively secure anchor location for the shunt structure 81 of the sensor implant device 80. Furthermore, the implant device 80 may be implanted at a position that is desirable in consideration of future re-crossing of the septal wall 18 for future interventions. Implantation of the sensor implant device 80 in the atrial septum wall 18 may advantageously allow for fluid communication between the left 2 and right 5 atria.

Interatrial shunting using the sensor implant device 80 may be well-suited for patients that are relatively highly sensitive to atrial pressure increases. For example, as pressure increases in the ventricles and/or atria and is applied against the myocardial cells, the muscles of the heart may generally be prone to contract relatively harder to process the excess blood. Therefore, as the ventricle dilates or stretches, for patients with compromised contractility of the ventricle, such patients may become more sensitive to higher pressures in the ventricle and/or atria because the heart may be unable to adequately respond or react thereto. Furthermore, increases in left atrial pressure can results in dyspnea, and therefore reduction in left atrial pressure to reduce dyspnea and/or reduce incidences of hospital readmission may be desirable through interatrial shunting. For example, when the ventricle experiences dysfunction such that is unable to accommodate build-up in fluid pressure, such fluid may backup into the atria, thereby increasing atrial pressure. With respect to heart failure, minimization of left ventricular end-diastolic pressure may be paramount. Because left ventricular end-diastolic pressure can be related to left atrial pressure, backup of fluid in the atrium can cause backup of fluid in the lungs, thereby causing undesirable and/or dangerous fluid buildup in the lungs. Interatrial shunting, such as using shunt devices in accordance with embodiments of the present disclosure, can divert extra fluid in the left atrium to the right atrium, which may be able to accommodate the additional fluid due to the relatively high compliance in the right atrium.

As with other embodiments, the sensor implant device 80 shown in FIG. 13 can include a sensor device 60 including a sensor transducer component 65 and a cylindrical (or other-shaped) housing 69. The sensor device is disposed, attached, and/or otherwise secured or to or associated with the sensor arm 82 in a manner such that the sensor transducer 65 is disposed in a channel area associated with the barrel/conduit portion 78 of the shunt structure 81, the relevant channel area being within the left atrium. The sensor arm 82 and sensor-retention portion 83 thereof may have any of the characteristics of sensor arms and associated sensor-retention portions disclosed herein in connection with any of the embodiments of the present disclosure.

Figure 14:
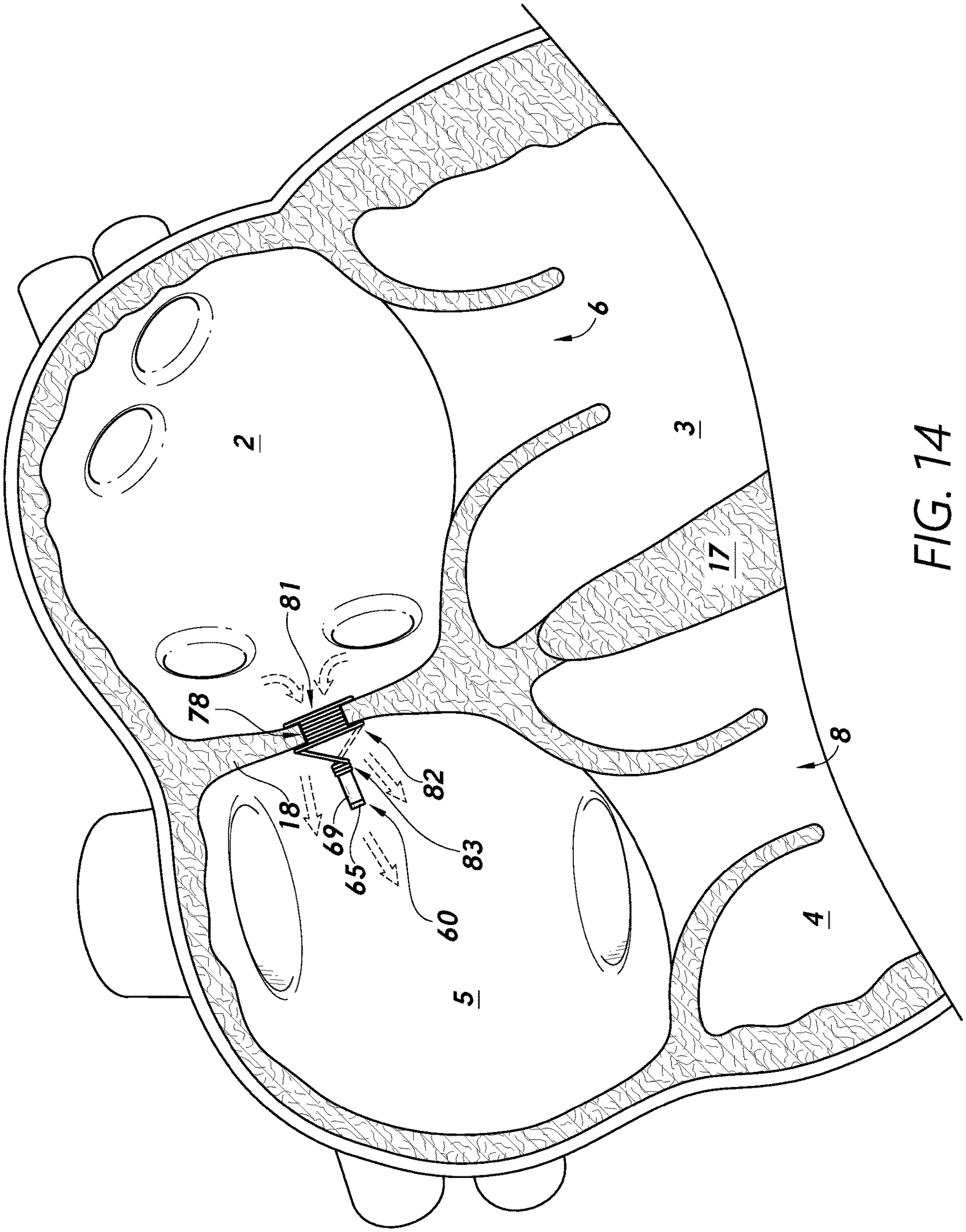
FIG. 14 shows a sensor implant device implanted in an atrial septum with a sensor of the device exposed in a right atrium in accordance with one or more embodiments.

FIG. 14 shows a sensor implant device 80 implanted in an atrial septum 18 with a sensor 60 of the device exposed in a right atrium 2 in accordance with one or more embodiments. As with other embodiments, the sensor implant device 80 shown in FIG. 14 can include a sensor device 60 including a sensor transducer component 65 and a cylindrical (or other-shaped) housing 69. The sensor device 60 is disposed, attached, and/or otherwise secured or to or associated with a sensor arm 82 of the shunt structure 81 of the implant device 80 in a manner such that the sensor transducer 65 is disposed in a channel area associated with the barrel/conduit portion 78 of the shunt structure 81, the relevant channel area being within the right atrium 2.

Figure 15:
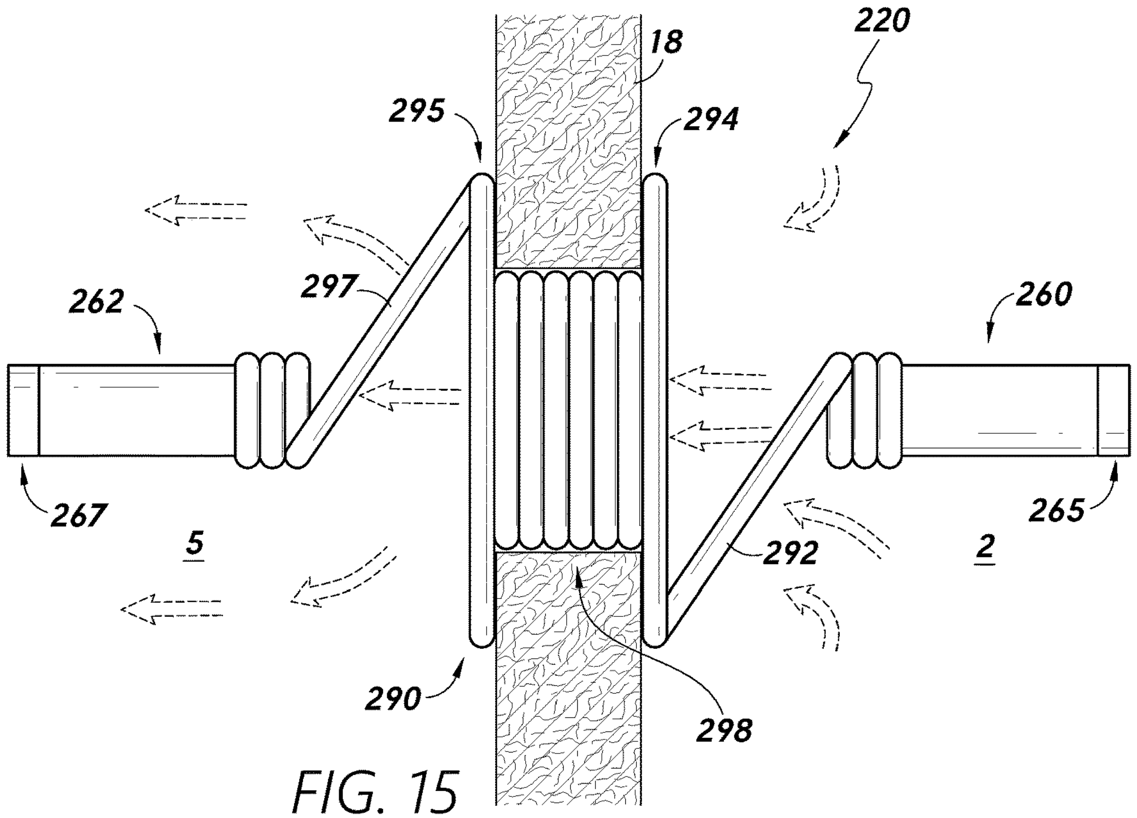
FIG. 15 shows a dual-sensor implant device implanted in a tissue wall in accordance with one or more embodiments.

FIG. 15 shows a dual-sensor implant device 220 implanted in an atrial septum 18 in accordance with one or more embodiments. Although certain embodiments are disclosed herein in the context of sensor implant devices including a single sensor device associated with a shunt structure, it should be understood that shunt sensor implant devices in accordance with aspects of the present disclosure may have any suitable or desirable number of sensor devices associated therewith. For example, the sensor implant device 220 shown in FIG. 15 includes two sensor devices 260, 262, wherein one of the sensor devices 260 is associated with a first sensor arm 292, whereas the other sensor device 262 is associated with a second sensor arm 297. The sensors 260, 262 are advantageously positioned, secured, and/or configured in a position/orientation such that respective sensor transducer components (265, 267) thereof are exposed in respective channel area(s) of the shunt structure 290 of the sensor implant device 220 on respective sides of the septum

18, as shown. For example, the senor arm 292 may emanate from a first flange 294, whereas the sensor arm 297 may emanate from a second flange 295, the flanges 294, 295 emanating from opposite axial sides of a barrel portion 298 of the shunt structure 290. Utilizing two or more sensors, with one or more sensors on each axial side/end of the relevant shunt structure, can provide improved shunt flow information in addition to atrial pressure information. Furthermore, where the sensor transducers of the two sensor devices face in opposite/opposing directions, as in the embodiment of FIG. 15, improved directional flow information may be derivable.

FIG. 15 shows the sensor implant device 220 implanted in the atrial septum wall 18 such that the first sensor 260 and associated sensor transducer 265 are exposed in the left atrium 2, whereas the second sensor 262 and associated sensor transducer 267 are exposed to the right atrium 5. In some embodiments of dual-sensor implant devices that may be similar in certain respects to the implant device 220, both the sensors may be exposed in the left atrium 2 or in the right atrium 5. With respect to multi-sensor shunt implant devices in accordance with aspects of the present disclosure, sensor transducers associated with at least one of the sensor devices may advantageously be disposed at least partially within a channel area associated with the relevant conduit/barrel structure. Furthermore, it should be understood that any description herein relating to the disposition/presence of a sensor transducer within a channel area associated with a shunt structure can be interpreted to mean that the sensor transducer is disposed wholly within the relevant channel area or partially within the channel area.

Although the illustration of FIG. 15 shows the two sensor devices 260, 262 being associated with sensor arms 292, 297 emanating from opposite axial sides/ends of the fluid conduit/barrel structure 298, such that the sensor devices are exposed on opposite sides of the tissue wall 18, it should be understood that dual-sensor shunt implant devices in accordance with aspects of the present disclosure may have sensor devices associated with any sensor arm/feature. For example, as an alternative to the particular illustrated embodiment of FIG. 15, the sensor implant device 220 may include sensor devices associated with sensor arms associated with and/or emanating from a common axial side of the conduit/barrel structure 298 and/or common anchor flange, such that both sensors are exposed on a common side of a tissue wall in which the sensor implant device 220 is implanted.

Figure 16:
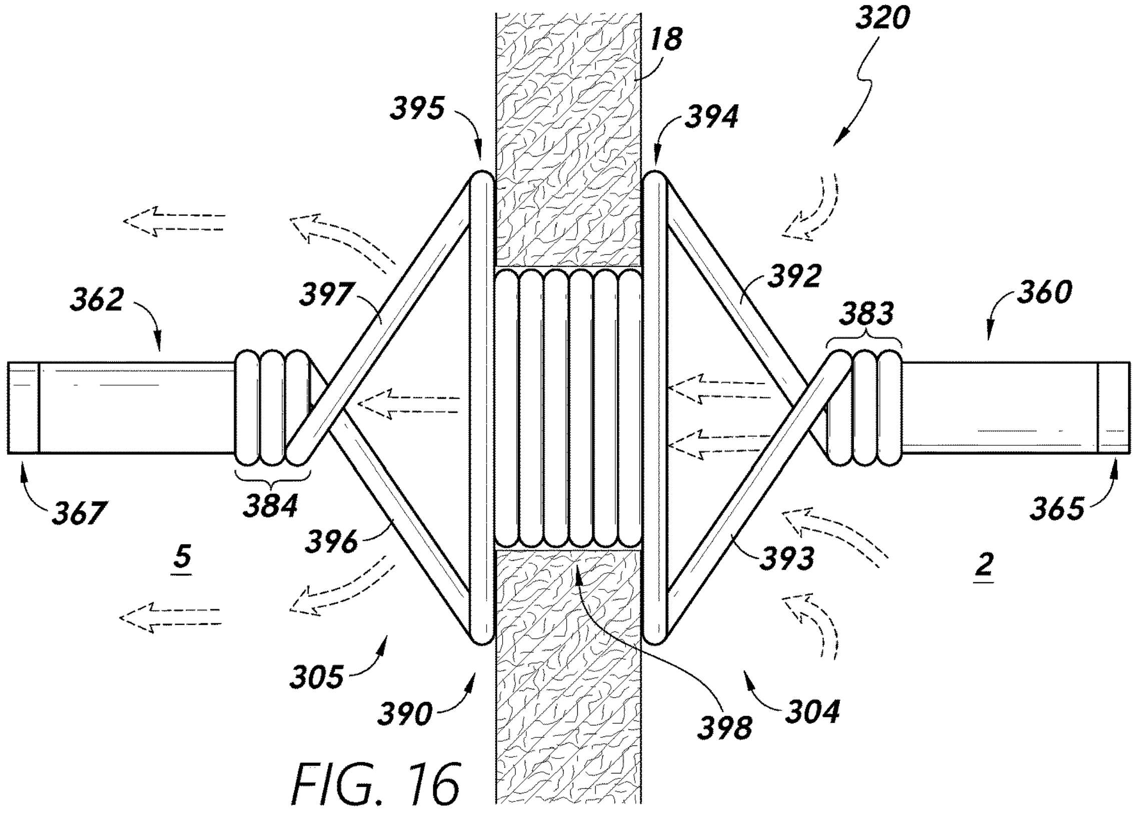
FIG. 16 shows a dual-sensor implant device implanted in a tissue wall in accordance with one or more embodiments.
Figures 1, 17:
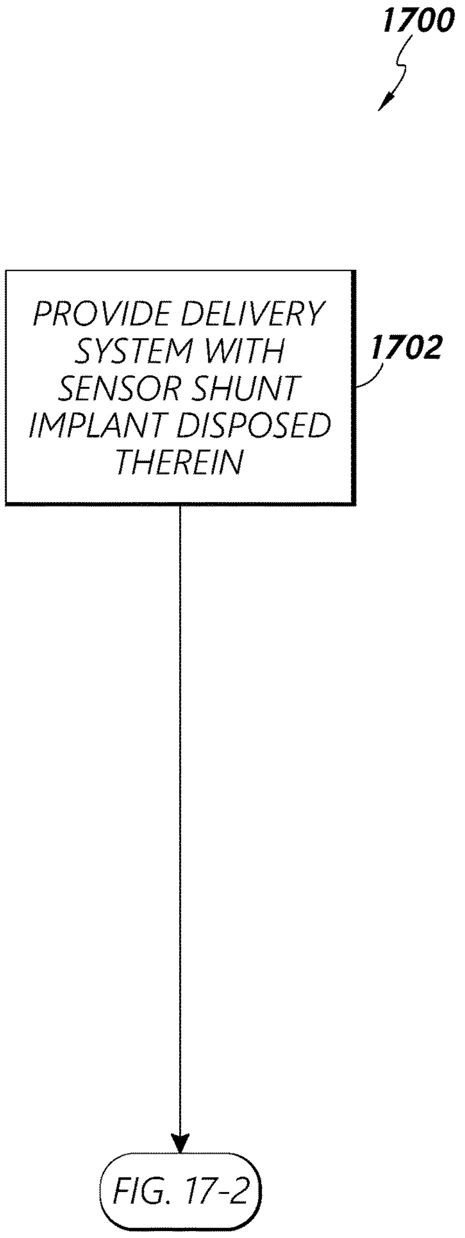

FIG. 16 shows a dual-sensor implant device 330 implanted in an atrial septum 18 in accordance with one or more embodiments. The sensor implant device 330 may be similar in any respect to the sensor implant device 220 shown in FIG. 15 and described above, with the exception that the sensor implant device 330 includes sensor-retention structures that comprise multiple sensor arms supporting each (or at least one) of the two sensor devices 360, 362.

The sensor implant device 330 includes two (or more) sensors 360, 362, each of which may be supported by two arms in a manner as described above in connection with FIGS. 11A and 11B. The sensor 360 is supported at least in part by a first sensor arm 392 on a given axial side 304 of the shunt structure 390. A second sensor 393 arm that may be similar to the first sensor arm 392, and may emanate from an opposite side and/or circumferential area of the flange 394 and/or shunt structure 390, may further be included as part of the shunt structure 390 and may advantageously provide a desirable degree of stability for retention of the sensor 360. One or more arms 396, 397 may likewise be included on the opposite axial side 305 of the shunt structure. Each of the sensor arms 392, 393, 396, 397 may be radially deflected, as described in detail above, to position the respective sensor device in a channel area of the shunt structure 390. Although two arms are shown associated with each of the axial sides of the shunt structure 390 in FIG. 16, it should be understood that embodiments of the present disclosure may have any suitable or desirable number of sensor arms on a given axial side of a shunt structure, including three arms, four arms, or more.

In some embodiments, the shunt structure 390 and/or the sensor arms 392, 393, 396, 397 are formed from multiple/separate wires, rather than a single common wire as with certain other embodiments. For example, the shunt structure 390 may be made up of at least two separate wires, which may be coiled/wound together to provide the shunt structure 390. In some such embodiments, both/all wires may traverse the barrel portion 398 and may each have an end on each axial side of the shunt structure 390. In some embodiments, two separate wires of the shunt structure 390 may be helical (i.e., wound/coiled) in the same direction (e.g., both clockwise or counterclockwise winding in a given axial direction), or may be wound/coiled in opposite directions.

In some embodiments, the two sensor arms 392, 393 associated with a given axial side 304 of the shunt structure 390 are associated with opposite ends of the same wire. For example, such wire may be wrapped around the sensor 360 in the sensor-retention portion 383 at the sensor arm 392, and traverse the flange 394, barrel 398, and flange 395 to the sensor arm 396, wherein the wire further wraps around the sensor 362 or otherwise is secured/attached to the sensor device 362 at the sensor-retention portion 384 and further forms the sensor arm 397 and traverses back through the flange 395, barrel 398, flange 394 and forms the sensor arm 393 and wraps around or otherwise secures or attaches to the sensor 360 on the side 304. In some embodiments, the sensor structure 390 comprises two wires, wherein opposite ends of each wire wrap around or otherwise are secured to the sensors 360, 362, respectively in the sensor-retention regions 383, 384.

Although FIGS. 15 and 16 are described in the context of sensor implant devices implanted in an atrial septum, it should be understood that, as with any other embodiment disclosed herein, such sensor implant devices may be implanted in any tissue wall or anatomy. Furthermore, the identified sides 304, 305 of the shunt structure 390 may be implanted on either side of an atrial septum or other wall.

FIGS. 17-1, 17-2, 17-3, 17-4, and 17-5 provide a flow diagram illustrating a process 1700 for implanting a sensor implant device in accordance with one or more embodiments. FIGS. 18-1, 18-2, 18-3, 18-4, and 18-5 provide images of cardiac anatomy and certain devices/systems corresponding to operations of the process 1700 of FIGS. 17-1, 17-2, 17-3, 17-4, and 17-5 in accordance with one or more embodiments.

Figures 1, 18:
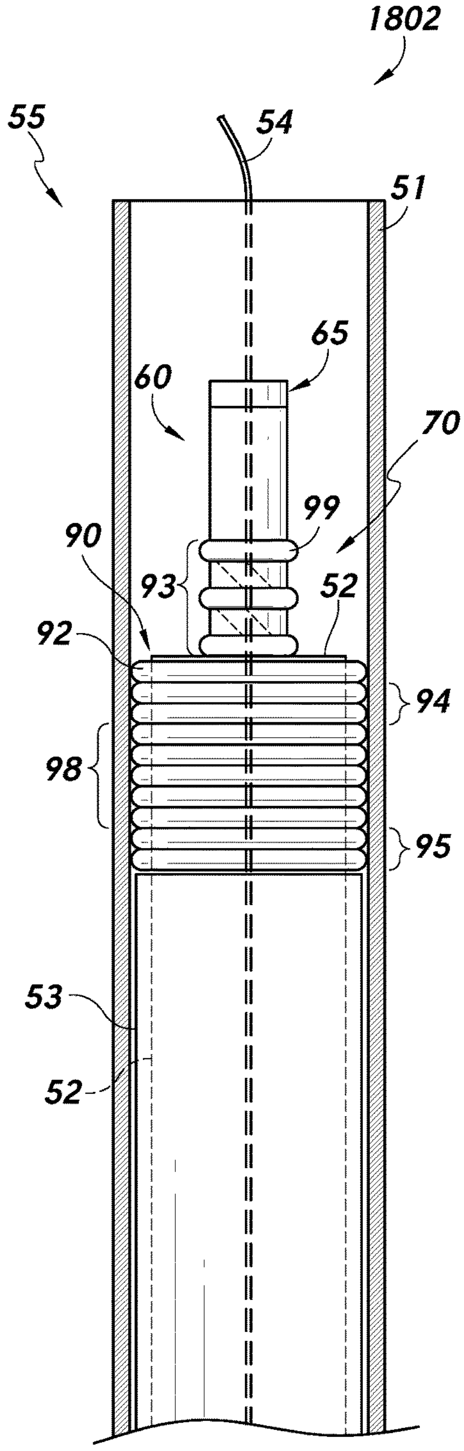
Figures 2, 17:
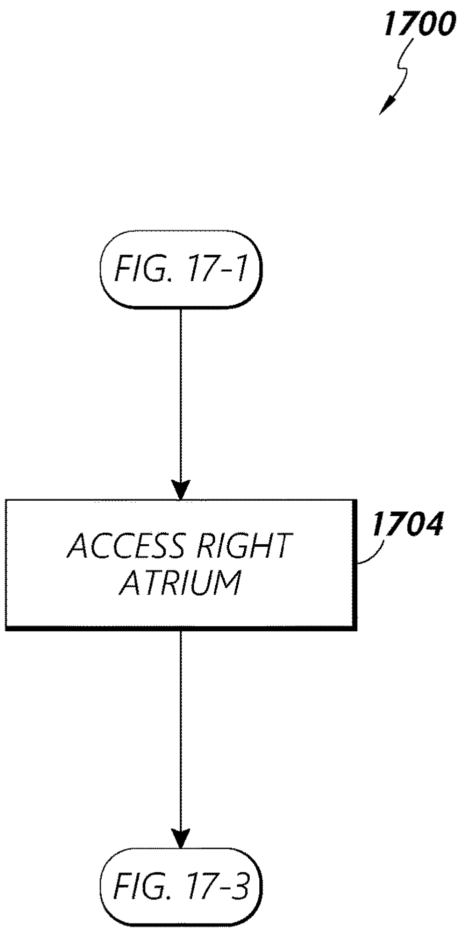
Figures 2, 18:
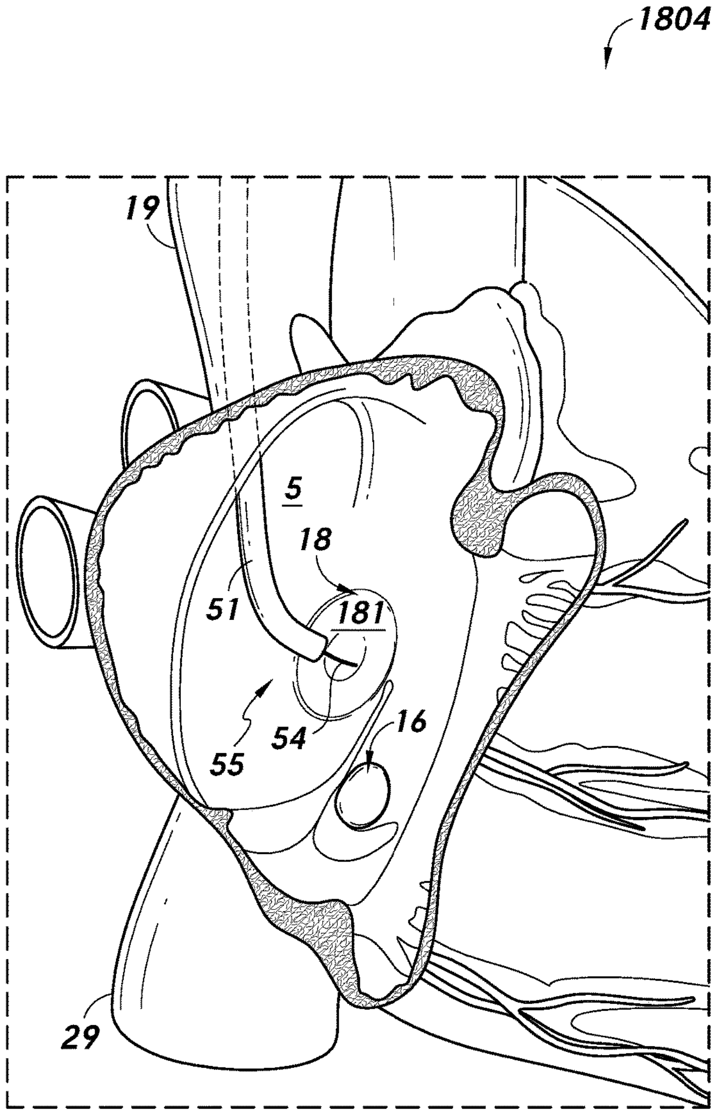
Figures 3, 18:
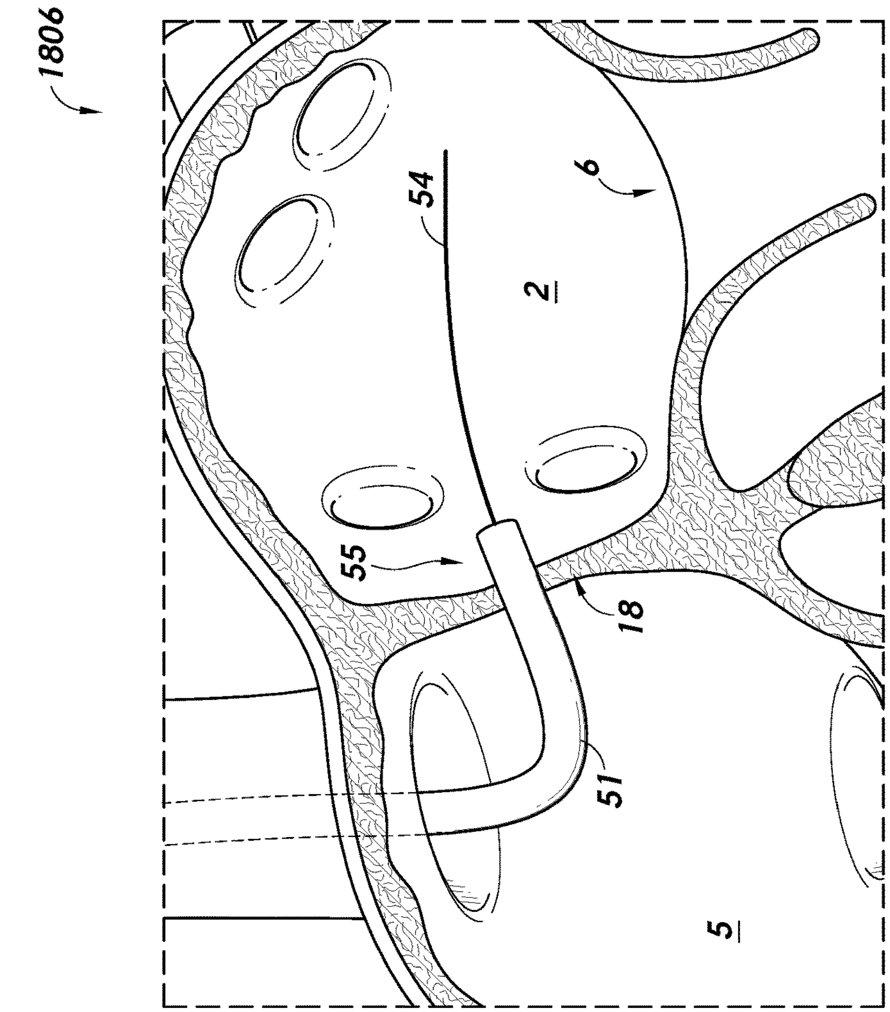
Figures 3, 17:
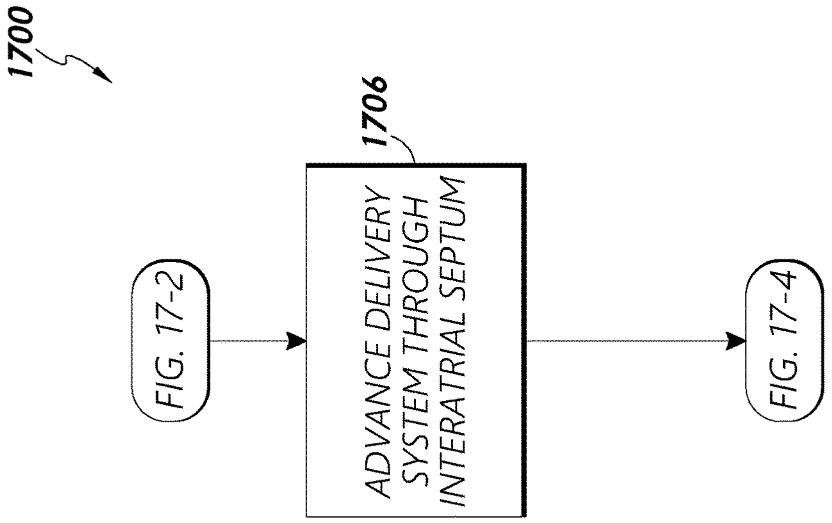
Figures 4, 18:
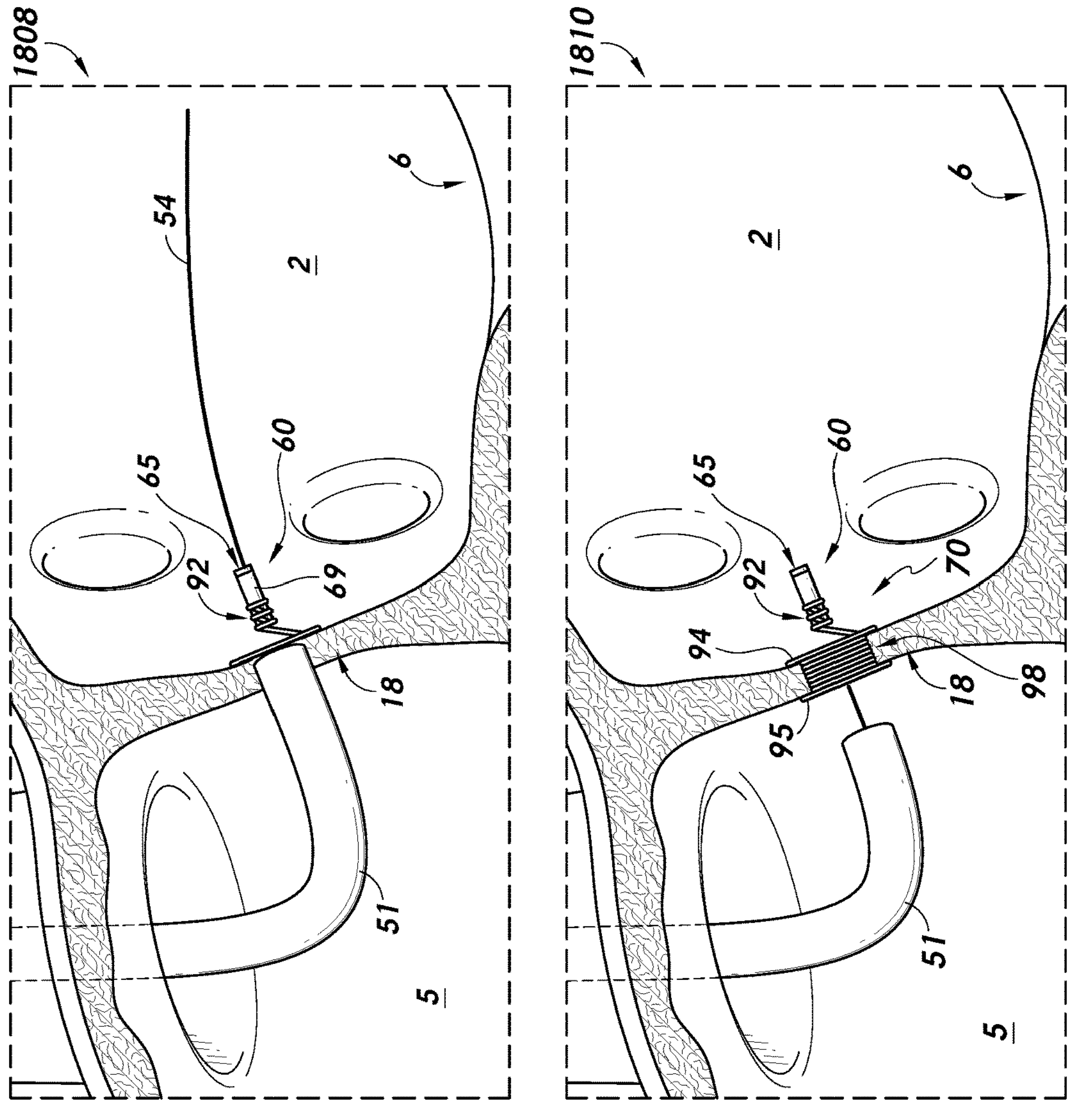
Figures 4, 17:
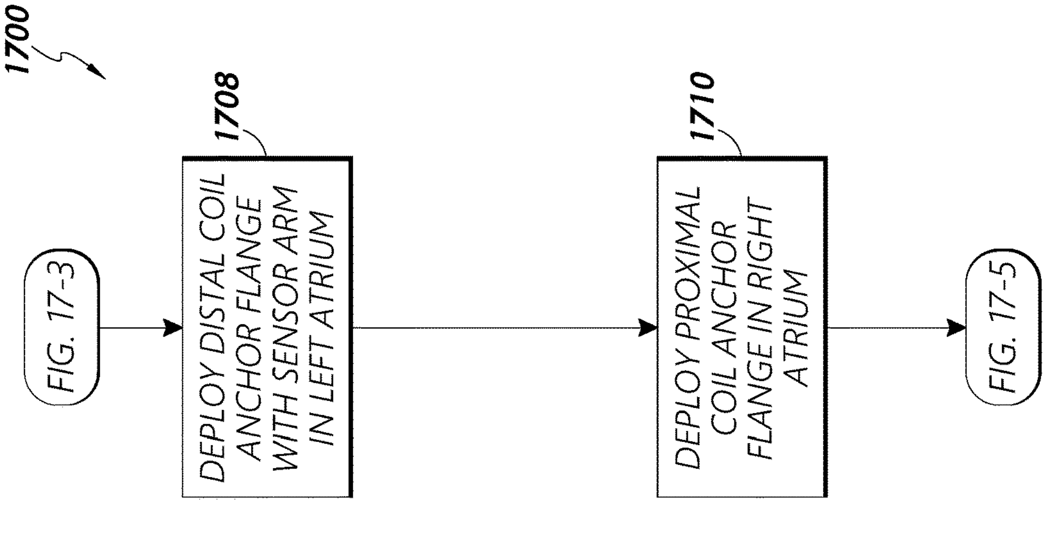
Figures 5, 17:
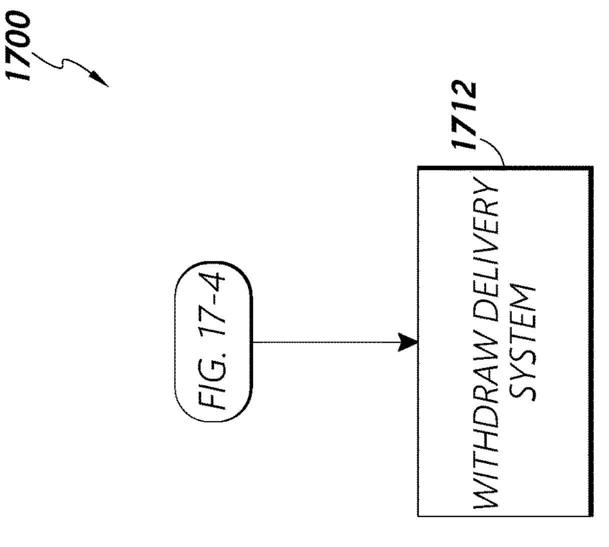
Figures 5, 18:
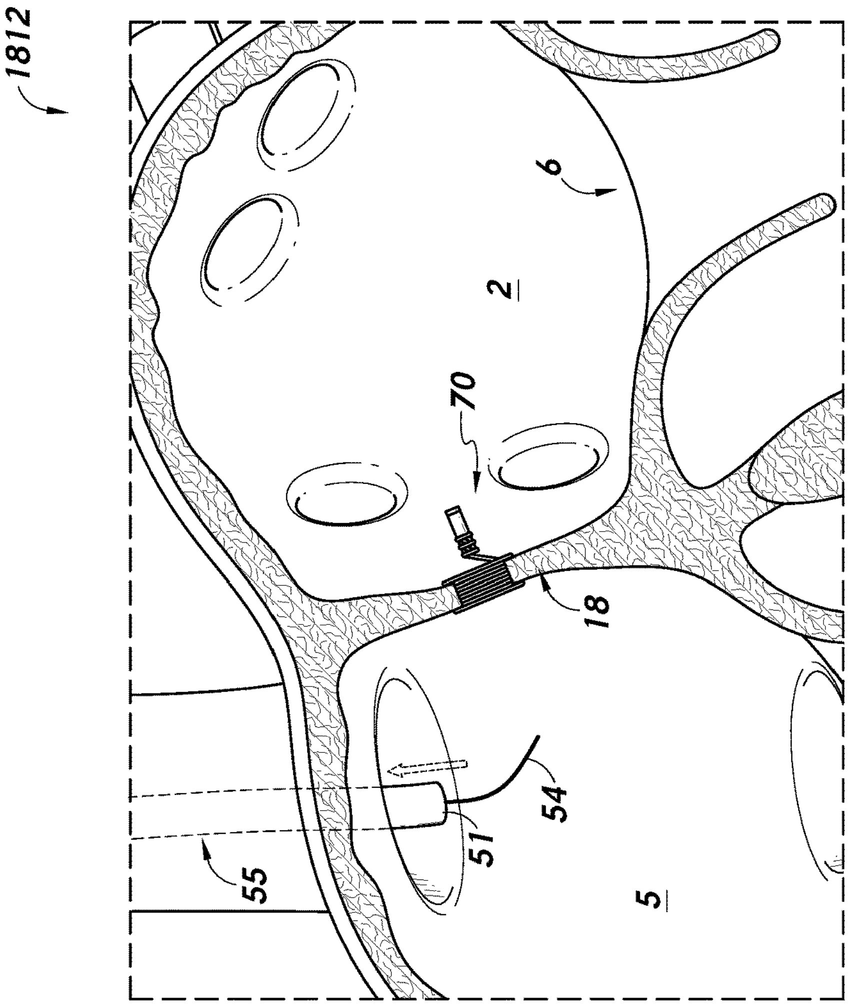

At block 1702, the process 1700 involves providing a delivery system 55 with a sensor implant device 70 disposed therein in a delivery configuration, such as a wireform shunt-type sensor implant device as disclosed in detail herein. Image 1802 of FIG. 18-1 shows a partial cross-sectional view of the delivery system 55 and sensor implant device 70 in accordance with one or more embodiments of the present disclosure. The image 1802 shows the sensor implant device 70 disposed within an outer sheath 51 of the delivery system 55. Although a particular embodiment of a delivery system is shown in FIG. 18-1, it should be understood that sensor implant devices in accordance with aspects of the present disclosure may be delivered and/or implanted using any suitable or desirable delivery system and/or delivery system components.

The illustrated delivery system 55 includes an inner catheter 52, which may be disposed at least partially within the outer sheath 51 during one or more periods of the process 1700. In some embodiments, the shunt structure 90 of the sensor implant device 70 may be wound/disposed at least partially around the inner catheter 52, wherein the shunt structure 90 is disposed at least partially within the outer sheath 51 during one or more periods of the process 1700. For example, the inner catheter 55 may be disposed within at least the barrel portion 98 of the shunt structure 90, as shown.

In some embodiments, the delivery system 51 may be configured such that a guidewire 54 may be disposed at least partially therein. For example, the guidewire 54 may run in the area of an axis of the sheath 51 and/or inner catheter 52, such as within the inner catheter 52, as shown. The delivery system 55 may be configured to be advanced over the guidewire 54 to guide the delivery system 55 to a target implantation site.

Although not shown in FIG. 18-1, in some embodiments, the delivery system 55 can include a tapered nosecone feature, which may be associated with a distal end of the sheath 51, catheter 52, and/or delivery system 55. Such nosecone feature(s) may be utilized to dilate an opening in a tissue wall into which the sensor implant device 70 is to be implanted, or through which the delivery system is to be advanced. Furthermore, a nosecone feature may facilitate advancement of the distal end of the delivery system 55 through the tortuous anatomy of the patient and/or within the outer delivery sheath or other conduit/path. In some embodiments, the delivery system may include a nosecone feature that comprises and/or is formed of multiple flap-type forms that can be urged/spread apart when the sensor implant device 70 and/or any portions thereof, the interior catheter 55, or other device(s) are advanced therethrough.

In some embodiments, the sensor implant device 70 may be disposed in the delivery system 55 with a sensor device 60, as described in detail herein, attached thereto or otherwise associated therewith. In some embodiments, the inner catheter 52 includes one or more sensor-accommodation features (not shown), such as one or more cut-outs, indentations, recesses, gaps, openings, apertures, holes, slits, or other features configured to accommodate the presence of the sensor device 60 and/or other feature(s) or aspect(s) of the implant device 70. Such sensor accommodation feature(s) may be longitudinal and circumferential cut-outs of the inner catheter 52, for example, and may be dimensioned to correspond to the size and/or profile of the sensor device and may allow for the sensor device to radially project into an inner diameter/space of the inner catheter 55. In some embodiments, as shown in image 1802, the sensor 60 and sensor-retention portion 93 of the sensor arm 92 may be disposed distally beyond the distal end of the inner catheter 52 when in the delivery configuration.

The sensor implant device 70 can be positioned within the delivery system 55 with a first/distal end thereof disposed distally with respect to the barrel 98 of the shunt structure 90. One or more of the distal coils/winds of the shunt structure 90 can be associated with and/or form a sensor arm 92 as described herein. Further, one or more of the winds/coils of the shunt structure 90 in a distal portion thereof can be associated with and/or form a distal flange 94 when deployed and expanded. A second/proximal end is positioned at least partially proximally with respect to the barrel 98 of the shunt structure 90 and/or the sensor device 60. One or more of the winds/coils of the shunt structure 90 in a proximal portion thereof can be associated with and/or form a proximal flange 95 when deployed and expanded.

The outer sheath 50 may be used to transport the sensor implant device 70 to the target implantation site. That is, the sensor implant device 70 may be advanced to the target implantation site at least partially within a lumen of the outer sheath 51, such that the sensor implant device 70 is held and/or secured at least partially within a distal portion of the outer sheath 51.

The delivery system 55 can further include a pusher 53, which may comprise an at least partially hollow tube configured to slide over the inner catheter 52, wherein distal advancement of the pusher 53 relative to the inner catheter 52 when the distal end of the pusher 53 is in contact with the proximal end of the shunt structure 90 causes the shunt structure 90 to be moved over/off the inner catheter 52.

At block 1704, the process 1700 involves accessing a right atrium 5 of a heart of a patient using the delivery system 55 with the sensor implant device 70 disposed therein. In some implementations, accessing the cardiac anatomy with the delivery system 55 may be performed following one or more procedures or steps to place the guidewire 54 and/or form and/or dilate an opening in the atrial septum 18, such as in the area of the fossa ovalis 1811, the details of which are omitted for convenience and clarity.

At block 1706, the process 1700 involves advancing the delivery system 55 into the left atrium 2 through the atrial septum 18. Access to the septum 18 and left atrium 2 via the right atrium 5 may be achieved using any suitable or desirable procedure. For example, various access pathways may be utilized in maneuvering guidewires and catheters in and around the heart to deploy an expandable shunt integrated or associated with a pressure sensor in accordance with embodiments of the present disclosure. In some embodiments, access may be achieved through the subclavian or jugular vein into the superior vena cava (not shown) and from there into the right atrium 5. Alternatively, the access path may start in the femoral vein and through the inferior vena cava (not shown) into the heart. Other access routes may also be used, each of which may typically utilize a percutaneous incision through which the guidewire and catheter are inserted into the vasculature, normally through a sealed introducer, and from there the system may be designed or configured to allow the physician to control the distal ends of the devices from outside the body.

In some implementations, the guidewire 54 is introduced through the subclavian or jugular vein, through the superior vena cava 19, and into the right atrium 5. In some implementations, the guidewire 54 can be disposed in a spiral configuration within the left atrium 2, which may help to secure the guidewire in place. Once the guidewire 54 provides a path, an introducer sheath may be routed along the guidewire 54 and into the patient's vasculature, such as with the use of a dilator. The delivery catheter may be advanced through the superior vena cava to the right atrium 5, wherein the introducer sheath may provide a hemostatic valve to prevent blood loss. In some embodiments, a deployment catheter may function to form and prepare an opening in the septum 18, and a separate placement delivery system 55, as shown, is used for delivery of the sensor implant device 70. In other embodiments, the delivery system 55 may be used as the both the puncture preparation and implant delivery catheter with full functionality. In the present application, the term "delivery system" is used to represent a catheter or introducer with one or both of these functions.

Advancement of the delivery system 55 through the septum 18 may or may not be facilitated by a nosecone or other feature of the delivery system 55. With the delivery system 55 advanced through the septum 18, the sheath 51 may be open in the left atrium to allow for deployment of the sensor implant device 70 therefrom. The guidewire 54 may be disposed as running through the opening in the septum 18 prior to penetration thereof by the sheath 51. The opening in the septum 18 may originally be formed using a needle (not shown) associated with the delivery system 55 or other delivery system implemented prior to block 1706. In some implementations, the opening in the septum 18 may have been previously dilated using a balloon dilator or other instrument.

At block 1708, the process 1700 involves deploying one or more distal coils of the shunt structure 90, such that the coil(s) expand to form the sensor arm 92 and distal flange 94 of the sensor implant device 90 on the left atrial side of the septum 18. Deploying the coil(s) of the shunt structure 90 can be performed at least in part by advancing a pusher or other component of the delivery system 55 relative to the sheath 51. The anchor arm 92 can have associated therewith a sensor device 60, wherein a sensor transducer 65 of the sensor device 60 is exposed within the left atrium 2 such that the sensor transducer 65 can be used to obtain signals indicating physiological parameters associated with the left atrium, such as pressure.

At block 1710, the process 1700 involves deploying one or more proximal coils of the shunt structure 90 such that the coil(s) expand to form the proximal flange 95 on the right atrium side of the septum 18 to thereby sandwich portions of the septal wall 18 between the distal 94 and proximal 95 flanges of the shunt structure 90. Such deployment of the coil(s) of the shunt structure 90 can be performed at least in part by advancing a pusher or other component of the delivery system 55 relative to the sheath 51.

At block 1712, the process 1700 involves withdrawing the delivery system 55, leaving the sensor implant device 70 implanted in the septum 18, thereby allowing blood flow to be shunted through the implant device 70 from the left atrium 2 into the right side of the heart. Although the implant device 70 is shown in the atrial septum 18, in some implementations, the implant device 70 may be positioned in a wall separating the left atrium 2 and coronary sinus, or between other cardiac chambers.

Figure 19:
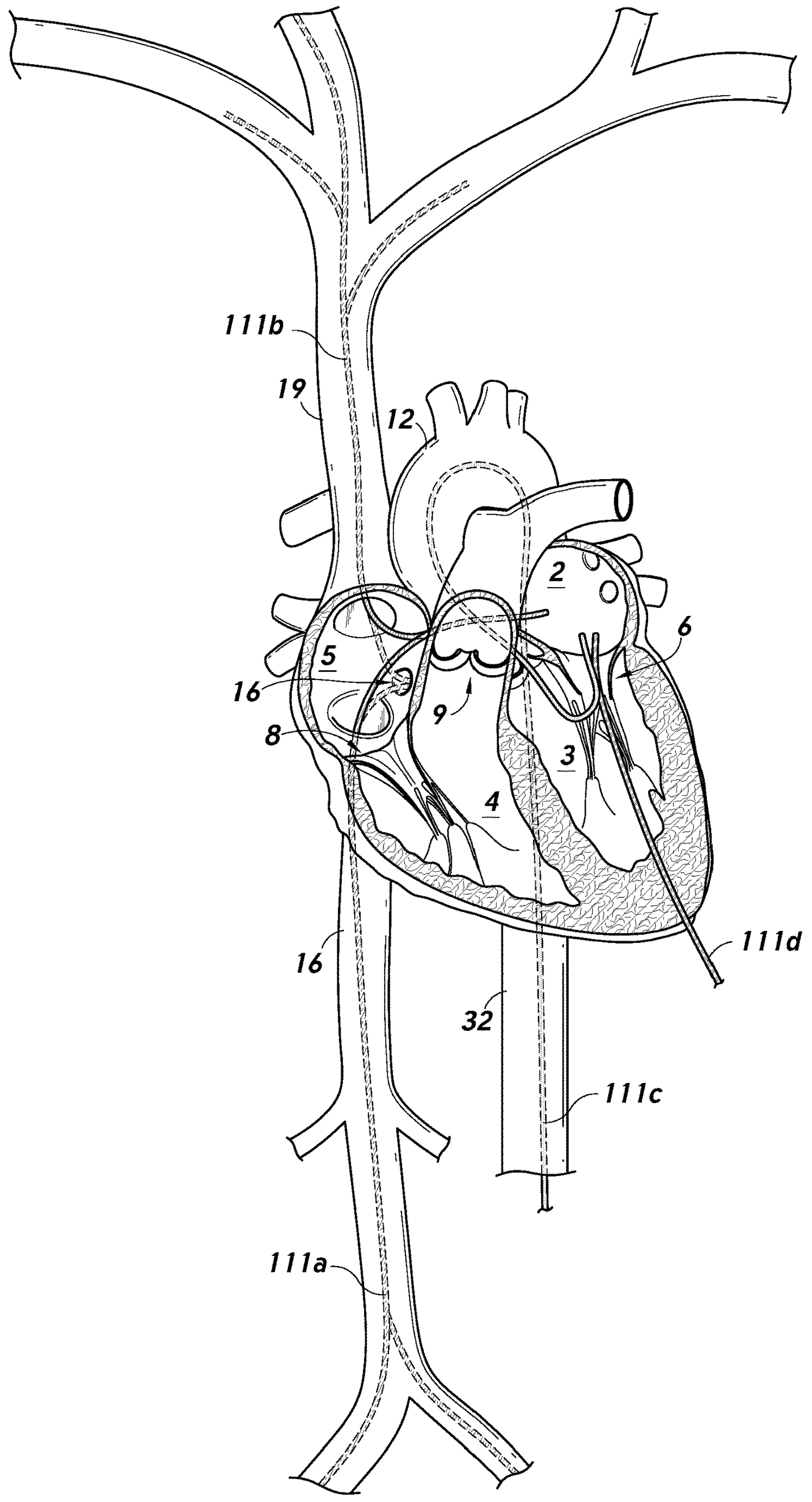
FIG. 19 is a cutaway view of a human heart and associated vasculature showing certain catheter access paths for pulmonary vein shunting procedures in accordance with one or more embodiments.

FIG. 19 shows various catheters 111 that may be used to implant sensor devices in accordance with aspects of the present disclosure. The catheters 111 can advantageously be steerable and relatively small in cross-sectional profile to allow for traversal of the various blood vessels and chambers through which they may be advanced en route to, for example, the right atrium 5, coronary sinus 16, left atrium 2 or other anatomy or chamber. Catheter access to the right atrium 5, coronary sinus 16, or left atrium 2 in accordance with certain transcatheter solutions may be made via the inferior vena cava 16 (as shown by the catheter 111*a*) or the superior vena cava 19 (as shown by the catheter 111*b*). Further access to the left atrium may involve crossing the atrial septum (e.g., in the area at or near the fossa ovalis).

Although access to the left atrium is illustrated and described in connection with certain examples as being via the right atrium and/or vena cavae, such as through a transfemoral or other transcatheter procedure, other access paths/methods may be implemented in accordance with examples of the present disclosure. For example, in cases in which septal crossing through the interatrial septal wall is not possible, other access routes may be taken to the left atrium 2. In patients suffering from a weakened and/or damaged atrial septum, further engagement with the septal wall can be undesirable and result in further damage to the patient. Furthermore, in some patients, the septal wall may be occupied with one or more implant devices or other treatments, wherein it is not tenable to traverse the septal wall in view of such treatment(s). As alternatives to transseptal access, transaortic access may be implemented, wherein a delivery catheter 111*c* is passed through the descending aorta 32, aortic arch 12, ascending aorta, and aortic valve 7, and into the left atrium 2 through the mitral valve 6. Alternatively, transapical access may be implemented to access the target anatomy, as shown by delivery catheter 111*d*.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A sensor implant device comprising:

a first sensor device; and a shunt body formed by a continuous helical wire coil, the helical wire coil defining:

a first anchor flange at a first axial end of the shunt body formed by a first segment of the helical wire coil having a first diameter;

a shunt fluid conduit adjacent to the first anchor flange, the shunt fluid conduit formed by a second segment of the helical wire coil having a second diameter that is less than the first diameter;

a second anchor flange at an opposite axial end of the shunt fluid conduit from the first anchor flange, the second anchor flange formed by a third segment of the helical wire coil having a third diameter that is greater than the second diameter; and a first sensor-support arm formed of a fourth segment of the helical wire coil continuing from an end of the second anchor flange, the first sensor-support arm continuing in a winding path that reduces to a coil having a fourth diameter that is less than the second diameter and is configured to hold the first sensor device over a channel area of the shunt fluid conduit at a position distally beyond an axial boundary of the second anchor flange such that an axial flow gap is presented between the axial boundary of the second anchor flange and the first sensor device to provide an unobstructed flow channel in a plane of the axial boundary of the second anchor flange.

2. The sensor implant device of claim 1, wherein, when in the position, the first sensor device overlaps an axis of the shunt fluid conduit.

3. The sensor implant device of claim 2, wherein, when in the position, a cylindrical body of the first sensor device is oriented coaxially with the shunt fluid conduit.

4. The sensor implant device of claim 1, wherein the first sensor-support arm is wrapped around a body of the first sensor device by a plurality of spaced winds around the body of the first sensor device.

5. The sensor implant device of claim 1, wherein the helical wire coil further comprises a fifth segment continuing from the end of the second anchor flange that forms a second sensor-support arm that winds in a common direction as the first sensor-support arm and extends from the second anchor flange over the channel area and holds the first sensor device.

6. The sensor implant device of claim 5, wherein the first sensor-support arm and the second sensor-support arm emanate from opposite circumferential sides of the second anchor flange shunt body.

7. The sensor implant device of claim 6, wherein both the first sensor-support arm and the second sensor-support arm both wrap around a circumference of a body of the first sensor device.

8. The sensor implant device of claim 1, wherein a cover is disposed around an outer diameter of at least a portion of the shunt fluid conduit formed by the second segment of the helical wire coil.

9. The sensor implant device of claim 1, wherein a cover is disposed around an inner diameter of at least a portion of the shunt fluid conduit formed by the second segment of the helical wire coil.

10. The sensor implant device of claim 1, further comprising a second sensor device coupled to a second sensor-support arm formed of a fifth segment of the helical wire coil continuing from an end of the second anchor flange, the second sensor-support arm being configured to hold the second sensor device over the channel area of the shunt fluid conduit.

11. The sensor implant device of claim 10, wherein a sensor transducer of the first sensor device and a sensor transducer of the second sensor device face in opposite directions.

12. The sensor implant device of claim 11, wherein the first sensor device and the second sensor device are coaxial.

13. A sensor implant device comprising:

a coil wireform winding in a first direction and comprising, in a deployed configuration:

a shunt body portion formed of a plurality of winds of coil of the coil wireform and having a first diameter;

a first flange anchor portion formed of one or more first winds of coil of the coil wireform emanating from a first axial end of the shunt body portion and having a second diameter that is greater than the first diameter;

a first sensor-support arm formed of a continuous wire extension integrated with and emanating from the first flange anchor portion, the first sensor-support arm following a first curved path in the first direction and deflected radially over a channel area radially defined by the shunt body portion, a distal portion of the first sensor-support arm including a sensor-retention means holding a first sensor device; and a second flange anchor portion formed of one or more second winds of coil of the coil wireform emanating from a second axial end of the shunt body portion;

wherein the first sensor-support arm is configured to hold the first sensor device at a position that is spaced beyond the first flange anchor portion such that an axial flow gap is presented between an axial boundary of the first flange anchor portion and a proximal-most portion of the first sensor device.

14. The sensor implant device of claim 13, further comprising a second sensor-support arm formed of a continuous wire extension integrated with and emanating from the second flange anchor portion, the second sensor-support arm following a second curved path in the first direction and deflected radially over the channel area defined by the shunt body portion.

15. The sensor implant device of claim 13, further comprising a second sensor-support arm emanating from the first flange anchor portion and deflected radially over the channel area defined by the shunt body portion, a distal portion of the second sensor-support arm being secured to the first sensor device.

16. The sensor implant device of claim 13, wherein the first sensor-support arm is deflected axially with respect to an axis of the shunt body portion at a greater angle than a deflection angle of the plurality of winds of coil of the shunt body portion.

17. The sensor implant device of claim 13, wherein the sensor-retention means comprises one or more winds of coil.

18. The sensor implant device of claim 13, wherein the sensor-retention means comprises a mechanical clip.

19. The sensor implant device of claim 13, further comprising a sealing means associated with the shunt body portion.

20. The sensor implant device of claim 19, wherein the sealing means comprises a fabric layer.

21. The sensor implant device of claim 13, wherein the coil wireform comprises shape memory material configured to assume the deployed configuration when deployed from a delivery catheter.

22. The sensor implant device of claim 21, wherein the coil wireform is configured to be compressed into a delivery configuration in which the shunt body portion and the first flange anchor portion have a third diameter that is smaller than the first diameter.

* * * * *